(12) United States Patent
Tang et al.

(10) Patent No.: US 12,390,530 B2
(45) Date of Patent: Aug. 19, 2025

(54) STIMULI RESPONSIVE BLOCK COPOLYMERS

(71) Applicant: Boston Scientific Scimed Inc., Maple Grove, MN (US)

(72) Inventors: Yiqing Tang, Guildford (GB); Nicolas Van Luc Busatto, Farnborough (GB); Francesco Cuda, Basingstoke (GB); Sean Leo Willis, Farnham (GB)

(73) Assignee: Boston Scientific Scimed, Inc., Maple Grove, MN (US)

( * ) Notice: Subject to any disclaimer, the term of this patent is extended or adjusted under 35 U.S.C. 154(b) by 48 days.

(21) Appl. No.: 17/992,662

(22) Filed: Nov. 22, 2022

(65) Prior Publication Data

US 2023/0158148 A1 May 25, 2023

Related U.S. Application Data

(60) Provisional application No. 63/282,349, filed on Nov. 23, 2021.

(51) Int. Cl.
  *A61K 47/32* (2006.01)
  *A61K 9/00* (2006.01)
  *A61K 45/06* (2006.01)

(52) U.S. Cl.
  CPC ............ *A61K 47/32* (2013.01); *A61K 9/0019* (2013.01); *A61K 45/06* (2013.01)

(58) Field of Classification Search
  CPC ...... A61K 47/32; A61K 9/0019; A61K 45/06; C08F 2438/01; C08F 293/005; A61L 2430/36; A61L 24/06
  See application file for complete search history.

(56) References Cited

U.S. PATENT DOCUMENTS

| | | | |
|---|---|---|---|
| 6,562,362 B1 | 5/2003 | Bae et al. | |
| 9,381,253 B2 * | 7/2016 | Johnson | A61K 47/58 |
| 2009/0103045 A1 | 4/2009 | Lai et al. | |
| 2013/0302392 A1 | 11/2013 | Mistry et al. | |
| 2013/0330278 A1 | 12/2013 | Gao et al. | |
| 2015/0216896 A1 * | 8/2015 | Berkland | A61K 31/785 424/78.37 |
| 2019/0117799 A1 * | 4/2019 | Xu | A61K 9/5138 |
| 2021/0338579 A1 | 11/2021 | Gao et al. | |

FOREIGN PATENT DOCUMENTS

| | | |
|---|---|---|
| CN | 103394305 A | 11/2013 |
| CN | 104945557 A | 9/2015 |
| JP | 2002-102331 A | 4/2002 |
| JP | 2004-512389 A | 4/2004 |
| JP | 2013-241567 A | 12/2013 |
| JP | 2017-534602 A | 11/2017 |
| JP | 2018-528962 A | 10/2018 |
| JP | 2019-528258 A | 10/2019 |
| WO | 2012166691 A1 | 12/2012 |
| WO | 2020243217 A1 | 12/2020 |

OTHER PUBLICATIONS

Mengxing Li. Thin films of stimuli-responsive hydrogels. Polymers. Université Pierre et Marie Curie, Paris VI, 2014. (Year: 2014).*
Bai et al; "pH-Responsive Dithiomal Eimade=Amplhillic Block Copolymer for Drug Delivery and Cellular Imaging," Journal of Colloid and Interface Science, vol. 552, pp. 439-447, 2019.
Fan et al; "Ultrasensitive (Co)polymers Based on Poly(methacrylamide) Structure with Fining-Tunable pH Responsive Value," Molecules, vol. 23, 1870, 9 pages.
Henn et al; "Tertiary-Amine-Containing Thermo- and pH-Sensitive Hydrophilic ABA Triblock Copolymers: Effect of Different Tertiary Amines on Thermally Induced Sol-Gel Transitions," Langmuir, vol. 30, pp. 2541-2550, 2014.
Huang et al; "Multi-Chromatic pH-Activatable (19) F-MRI Nanoprobes with Binary ON/OFF pH Transitions and Chemical Shift Barcodes," Agnew Chem Int Ed Engl. vol. 52, Issue 31, pp. 8074-8078, Jul. 29, 2013.
Li et al; "Non-covalent Interactions in Controlling pH-Responsive Behaviors of Self-Asebled Nanosystems," Polym Chem, vol. 7, Issue 38, pp. 5949-5956, Oct. 14, 2016.
Ma et al; "Ultra-pH-Sensitive Nanoprobe Library with Broad pH Tunability and Fluorescence Emissions," Journal of the American Chemical Society, vol. 136, pp. 11085-11092, 2014.
Wang et al; "A Nanobuffer Reporter Library for Fine-Scale Imaging and Pertubation of Endocytic Organelles," Nature Communcations, 6 8524, pp. 1-11, 2015.

(Continued)

*Primary Examiner* — Frederick F Krass
*Assistant Examiner* — Abdulrahman Abbas
(74) *Attorney, Agent, or Firm* — Seager, Tufte & Wickhem, LLP

(57) ABSTRACT

In various embodiments, the present disclosure pertains to compositions for medical use. In some embodiments, the compositions comprise an aqueous solution of a block copolymer that comprises one or more poly(N-isopropylamino acrylamide) blocks and one or more poly(2-(di-($C_{1-5}$)alkylamino) ($C_{1-5}$)alkyl methacrylate) blocks. In some embodiments, the compositions are in liquid form at 25° C. Other embodiments pertain to methods that comprise delivering such compositions to a patient.

20 Claims, 8 Drawing Sheets

(56) References Cited

OTHER PUBLICATIONS

Zhou et al; "Multicolored pH-Tunable and Activitable Fluorescence Nanoplatform Responsive to Physiologic pH Stimuli," J Am Chem Soc. Volume 134, Issue 18, pp. 7803-7811, May 9, 2012.
Zhou et al; "Tunable, Ultra-Sensitive pH Responsive Nanoparticles Targeting Specific Endocytic Organelles in Living Cells," Agnew Chem Int Ed Engl vol. 50, Issue 27, pp. 6109-6114, Jun. 27, 2011.
Zhu et al; "Synthesis of Tertiary Amine-Based pH-Responsive Polymers by RAFT Polymerization," Journal of Polymer Science, Part A: Polymer Chemistry, vol. 53, pp. 1010-1022, 2015.
Pogany et al; "Light-Sensitive Vinyl Polymers," Plaste und Kautschuk, vol. 10, Issue 12, pp. 728-730, 1963. [Abstract Only].
International Search Report and Written Opinion dated Mar. 27, 2023 for International Application No. PCT/US2022/050764.

\* cited by examiner

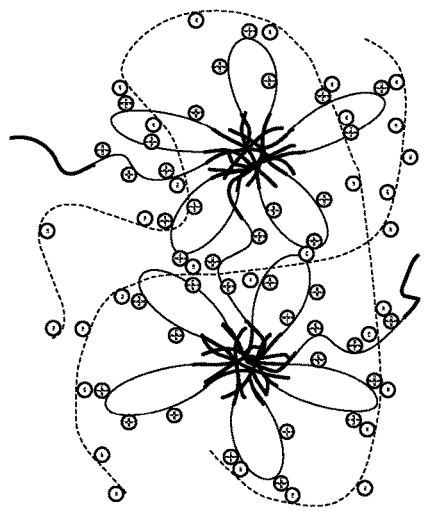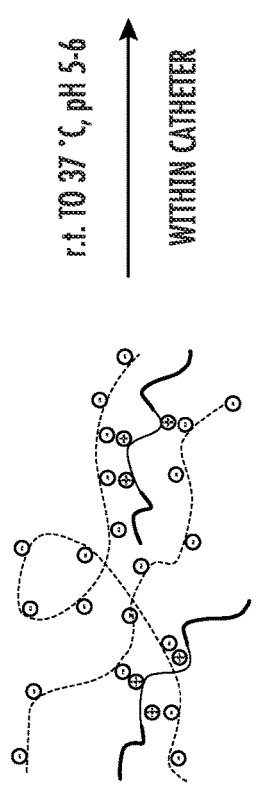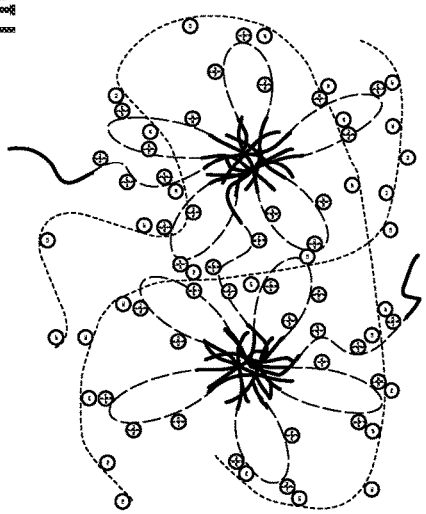

STIMULI RESPONSIVE BLOCK COPOLYMERS

CROSS-REFERENCE TO RELATED APPLICATIONS

This application claims the benefit of priority of U.S. Provisional Application No. 63/282,349, filed Nov. 23, 2021, the entire disclosure of which is hereby incorporated by reference herein for all purposes.

FIELD

The present disclosure relates to stimuli responsive block copolymers, to compositions containing such stimuli responsive block copolymers, and to methods of using such stimuli responsive block copolymers. The stimuli responsive block copolymers of the present disclosure are useful, for example, in various biomedical applications, including embolization.

BACKGROUND

Liquid embolic systems have gained increasing acceptance as effective agents for the embolization or filling of neural and peripheral diseases, such as hyper-vascular tumors, arteriovenous malformations, aneurysms, and endoleaks. DMSO solvent based technologies that are used in commercial products or products being developed, such as Onyx® (Medtronic), Squidperi™ (Emboflu/Balt), PHIL™ (Terumo), and Easyx™ (Antia AG), are based on the solubility changes of embolic polymers during transition from DMSO solvent to water in blood. They have limitations due to the intrinsic toxicity of DMSO which can cause tissue necrosis and vessel spasm. The presence of DMSO in the formulation can also result in the patient observing a strong odor similar to garlic after the procedure and this means each patient needs additional paperwork, such as Informed Consent, to make them aware of the potential side effects.

An aqueous based system has a lot of appeal to physicians and patients in this area since it eliminates DMSO. It also has the potential of greater biocompatibility and ease of use. It could also have the potential for drug loading applications, if desirable, as well as a bland embolic in a range of indications.

Several prominent aqueous based products have been through development and preclinical trials. For example, the polyelectrolyte GPX™ system (Fluidx Medical) uses charge interaction generated coacervates from electrostatically condensed, oppositely charged polyelectrolytes, polycationic salmine sulfate (Sal) and polyanionic sodium inositol hexaphosphate (IP6). A specific property of the polyelectrolyte complex is the charge interaction between polymer chains could be shielded by high ionic strength NaCl solution (1200 mM), which results in a clear, homogeneous, low viscosity fluid. The subsequent release of NaCl during in vivo delivery leads to a sol-gel transition to high viscosity coacervates. Tantalum powder is mixed with the formulation to required radiopacity under fluoroscope. The Obsidio hydrogel is a novel bioengineered tantalum-loaded nanocomposite gel embolic material (Ta-GEM). The system is formulated by mixing Gelatin (Type A, 18%), silicate nanoplatelets (Laponite XLG, 9%), ultrapure water and tantalum powder (2 um 20%, w/w). The disk-like Laponite nanoplatelets possess negative charges on the two faces, which can interact with positive charged Gelatin and form complexed gel structure. Other aqueous hydrogels reported are PuraMatrix™ which is a polypeptide hydrogel, and SELP (Silk-elastin-like Protein Polymer, University of Utah), a temperature sensitive system.

SUMMARY

In various embodiments, the present disclosure pertains to compositions for medical use. The compositions comprise a block copolymer that comprises one or more poly(N-isopropylamino acrylamide) blocks and one or more poly(2-(di-($C_{1-5}$)alkylamino)($C_{1-5}$)alkyl methacrylate) blocks, wherein each $C_{1-5}$ alkyl group is independently selected from methyl, ethyl, propyl, butyl and pentyl groups. In some embodiments, each of the $C_{1-5}$ alkyl groups is the same as the other.

In some embodiments, the compositions comprise an aqueous solution of a block copolymer that comprises one or more poly(N-isopropylamino acrylamide) blocks and one or more poly(2-(di-($C_{1-5}$)alkylamino)ethyl methacrylate blocks, wherein each $C_{1-5}$ alkyl group is independently selected from methyl, ethyl, propyl, butyl and pentyl groups. In some embodiments, each of the $C_{1-5}$ alkyl groups is the same as the other.

In various embodiments, which can be used in conjunction with the above embodiments, the one or more poly(2-(di-($C_{1-5}$)alkylamino)($C_{1-5}$)alkyl methacrylate) blocks in the block copolymer are poly(2-(di-($C_{3-5}$)alkylamino)ethyl methacrylate) blocks, and more typically are poly(2-(dibutylamino)ethyl methacrylate) blocks.

In various embodiments, which can be used in conjunction with the above embodiments, the compositions are in liquid form at 25° C.

In various embodiments, which can be used in conjunction with the above embodiments, the compositions have a pH ranging from 1 to 7.4, typically ranging from 4.5 to 6.5, and more typically ranging from 5 to 6.

In various embodiments, which can be used in conjunction with the above embodiments, the compositions become a gel when injected (e.g., at 20-25° C.) into phosphate buffered saline having pH 7.4 and a temperature of 37° C.

In various embodiments, which can be used in conjunction with the above embodiments, the compositions become a gel when injected (e.g., at 20-25° C.) into a vasculature of a patient (e.g., a mammalian patient such as a human).

In various embodiments, which can be used in conjunction with the above embodiments, the block copolymer is a triblock copolymer having two poly(N-isopropylamino acrylamide) blocks and one poly(2-(di-($C_{1-5}$)alkylamino) ($C_{1-5}$)alkyl methacrylate) block, more typically, two poly (N-isopropylamino acrylamide) blocks and one poly(2-(di-($C_{3-5}$)alkylamino)ethyl methacrylate) block.

In various embodiments, which can be used in conjunction with the above embodiments, the block copolymer is a triblock copolymer having one poly(N-isopropylamino acrylamide) block and two poly(2-(di-($C_{1-5}$)alkylamino)($C_{1-5}$)alkyl methacrylate) blocks, more typically, one poly(N-isopropylamino acrylamide) block and two poly(2-(di-($C_{3-5}$)alkylamino)ethyl methacrylate) blocks.

In various embodiments, which can be used in conjunction with the above embodiments, each of the one or more poly(N-isopropylamino acrylamide) blocks in the bock copolymer ranges from 5 to 1000 monomer units in length, more typically, 100 to 600 monomer units in length.

In various embodiments, which can be used in conjunction with the above embodiments, each of the one or more poly(2-(di-($C_{1-5}$)alkylamino)($C_{1-5}$)alkyl methacrylate)

blocks in the block copolymer range from 10 to 500 units in length, more typically, 50 to 300 monomer units in length.

In various embodiments, which can be used in conjunction with the above embodiments, the block copolymer ranges from 2000 to 500,000 Da in number average molecular weight.

In various embodiments, which can be used in conjunction with the above embodiments, the block copolymer is present in the compositions in a concentration ranging from 1 to 50% wt/wt with respect to the weight of the composition.

In various embodiments, which can be used in conjunction with the above embodiments, the compositions have a viscosity ranging from 10 mPa·s to 5000 mPa·s when measured at a shear rate 50 1/s at a temperature of 25° C.

In various embodiments, which can be used in conjunction with the above embodiments, the block copolymer further comprises an additional polymer block ranging from 1 to 500 monomer units in length that comprises amine groups. For example, the amine groups may be selected from aminoalkyl groups, alkylaminoalkyl groups and dialkylaminoalkyl groups, among others.

In various embodiments, which can be used in conjunction with the above embodiments, the compositions further comprise, in addition to the block copolymer, an anionic polymer that comprises negatively charged groups selected from sulfonate groups, sulfate groups, phosphate groups, phosphonate groups and carboxylate groups, among others.

In various embodiments, which can be used in conjunction with the above embodiments, the anionic polymer has a number average molecular weight ranging from 1000 to 5,000,000 Da.

In various embodiments, which can be used in conjunction with the above embodiments, the anionic polymer is present in an amount ranging from 0.1 to 50% wt/wt with respect to the weight of the compositions.

In various embodiments, which can be used in conjunction with the above embodiments, the anionic polymer is selected from sulfonate polymers, polyphosphates, poly(carboxylic acids) and negatively charged polysaccharides, among others.

In various embodiments, which can be used in conjunction with the above embodiments, the compositions further comprise an imaging agent. For instance, the imaging agent may be a radiocontrast agent, which may, for example, comprise metallic particles in some cases.

In various embodiments, which can be used in conjunction with the above embodiments, the compositions further comprise an inorganic salt such as sodium chloride or potassium chloride, among others. The inorganic salt may be present in a concentration ranging from 0.2 M to 5.0 M, more typically from 0.5 M to 2.0 M, among other possible values.

In various embodiments, which can be used in conjunction with the above embodiments, the compositions further comprise a therapeutic agent.

In various embodiments, which can be used in conjunction with the above embodiments, the compositions are provided in a vial or syringe barrel.

In various embodiments, the present disclosure pertains to methods that comprise delivering compositions in accordance to any of the above embodiments to a patient.

In some embodiments, the methods are methods of treatment and wherein the composition is delivered into a vasculature of the patient. For example, the method of treatment may be selected from a methods of treating tumors, methods of treating arteriovenous malformations, methods of treating aneurisms, methods of treating endoleaks, methods of treating gastrointestinal bleeding, or methods of treating bleeding caused by disease or trauma, among others.

In some embodiments, the methods comprise delivering the compositions into the patient as a fiducial marker.

In some embodiments, the methods comprise delivering the compositions between a first tissue and a second tissue of the patent, thereby spacing the first tissue from the second tissue.

In various embodiments, the present disclosure pertains to use of the compositions of any of the above embodiments as embolic agents, fiducial markers, tissue bulking agents, tissue-spacing materials, or therapeutic agent depots, among others.

BRIEF DESCRIPTION OF THE DRAWINGS

FIGS. 3A-3C are schematic illustrations of (a) a phase change during protonated triblock copolymer mixing with poly(2-acrylamido-2-methylpropane sulfonate) (polyAMPS) to form coacervates (FIG. 3A), (b) a temperature increase introducing NIPAAM aggregation (FIG. 3B), and (c) an in vivo pH change causing partial deprotonation of DBA and enhanced gel hydrophobicity (FIG. 3C), in accordance with an embodiment of the present disclosure.

FIG. 12A corresponds to pre-embolization. FIG. 12B corresponds to post-embolization. FIG. 12C corresponds to post-embolization injection of contrast.

FIG. 13A corresponds to pre-embolization. FIG. 13B corresponds to post-embolization. FIG. 13C corresponds to post-embolization injection of contrast.

DETAILED DESCRIPTION

Figure 1:
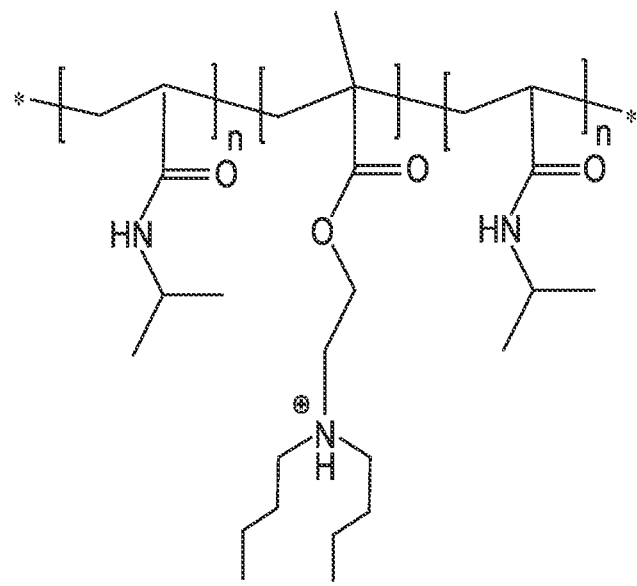
FIG. 1 is a schematic illustration of a poly(N-isopropylamino acrylamide)-poly(2-(dibutylamino)ethyl methacrylate)-poly(N-isopropylamino acrylamide) triblock copolymer, also referred to herein as a NIPAAM-DBA-NIPAAM triblock copolymer, pNIPAAM-pDBA-pNIPAAM triblock copolymer, or pNIPAAM-b-pDBA-b-pNIPAAM triblock copolymer.

In various aspects, the present disclosure pertains to compositions for medical use that comprise a block copolymer that comprises one or more poly(N-isopropylamino acrylamide) blocks and one or more poly(2-(di-($C_{1-5}$)alkylamino)($C_{1-5}$)alkyl methacrylate) blocks, wherein each $C_{1-5}$ alkyl group is independently selected from methyl, ethyl, propyl (where propyl includes n-propyl and isopropyl), butyl (where butyl includes n-butyl, isobutyl, sec-butyl and tert-butyl) and pentyl (where pentyl includes n-pentyl, tert-pentyl, neopentyl, isopentyl, sec-pentyl, 3-pentyl, sec-isopentyl, active pentyl) groups. In various aspects, the one or more poly(2-(di-($C_{1-5}$)alkylamino)($C_{1-5}$)alkyl methacrylate) blocks are poly(2-(di-($C_{1-5}$)alkylamino)ethyl methacrylate) blocks are and, more typically, are poly(2-(dibutylamino) ethyl methacrylate) blocks.

Such compositions include liquid compositions suitable for injection into the body. The compositions of the present disclosure may be provided in a vial or syringe barrel. In some embodiments, the composition in the vial or syringe barrel may be a liquid composition, for example, an aqueous liquid composition. In some embodiments, the composition in the vial or syringe barrel may be a dry composition to which a suitable fluid such as water for injection, dextrose 5% in water (D5W), saline, a buffer such as phosphate buffered saline, etc. can be added to form a liquid composition. In some embodiments, the vial or syringe may be stored under refrigerated conditions at a temperature ranging from 2-8° C. The compositions of the present disclosure may be provided in sterile form.

In various embodiments, the compositions of the present disclosure are liquid compositions that form a gel material (also referred to herein as a hydrogel material or a solidified material) in situ upon injection into the body. Such liquid compositions include liquid compositions that are capable of gel formation in response to in vivo conditions. In various embodiments, the liquid compositions form gels in response to both a change in pH and a change in temperature.

In various embodiments, the compositions of the present disclosure are in liquid form at room temperature (e.g., at or below 25° C., or at or below 30° C. in some embodiments), and may have a pH that is less than 7.0, typically ranging from 4.5 to 6.5, and more typically ranging from 5 to 6. After delivery to the body of a patient (e.g., to in vivo conditions where the temperature is about 37° C. and the pH is about 7) the liquid compositions spontaneously form a gel.

Such liquid compositions can be used in a number of medical applications, including use as liquid embolic compositions, fiducial markers, tissue-bulking materials, tissue-spacing materials, and depots which comprise a therapeutic agent and from which the therapeutic agent elutes into the surrounding tissue.

In embodiments wherein the liquid compositions of the present disclosure are injected into the body of a subject, the liquid compositions may be adapted to pass through the particular delivery device employed for the injection, preferably, with manual pressure. For example, in a typical injection, with the thumb pushing on the plunger and the ipsilateral index and middle fingers stabilizing flanks of the syringe barrel, an injection force of less than 50 N is preferred. The desired viscosity level will typically be dependent on the procedure and the delivery method. For direct injection with a needle and syringe, the amount of pressure required will depend, for example, on the gauge of the needle. Similarly, for injection via catheter, the amount of pressure required will depend, for example, upon the catheter internal diameter.

In some embodiments, the liquid compositions of the present disclosure have a viscosity ranging from 10 mPa·s or less to 5000 mPa·s or more when measured at shear rate 50 1/s at a temperature of 25° C. For example the compositions may have a viscosity ranging anywhere from 10 mPa·s to 25 mPa·s to 50 mPa·s to 100 mPa·s to 250 mPa·s to 500 mPa·s to 1000 mPa·s to 2500 mPa·s to 5000 mPa·s at a shear rate 50 1/s and a temperature 25° C.

As previously noted, the compositions of the present disclosure comprise a block copolymer that comprises one or more poly(N-isopropylamino acrylamide) blocks and one or more poly(2-(di-($C_{1-5}$)alkylamino)($C_{1-5}$)alkyl methacrylate) blocks, more typically, one or more poly(N-isopropylamino acrylamide) blocks and one or more poly(2-(di-($C_{3-5}$)alkylamino)ethyl methacrylate) blocks, for example, one or more poly(N-isopropylamino acrylamide) blocks and one or more poly(2-(dibutylamino)ethyl methacrylate) blocks.

In some embodiments, each of the poly(N-isopropylamino acrylamide) block(s) range(s) in length from 5 monomer units or less to 1000 monomer units or more, for example, ranging anywhere from 5 to 10 to 25 to 50 to 100 to 300 to 600 to 1000 monomer units (i.e., ranging between any two of the preceding numerical values). In certain beneficial embodiments, each of the poly(N-isopropylamino acrylamide) block(s) is greater than 100 monomer units in length and less than 600 monomers in length.

In some embodiments, each of the one or more poly(2-(di-($C_{1-5}$)alkylamino)($C_{1-5}$)alkyl methacrylate) blocks range in length from 10 monomer units or less to 500 monomer units or more, for example, ranging anywhere from 10 to 25 to 50 to 75 to 100 to 200 to 250 to 300 to 500 monomer units in length. In certain beneficial embodiments, each of the poly(2-(di-($C_{1-5}$)alkylamino)($C_{1-5}$)alkyl methacrylate) blocks is greater than 50 monomer units in length and less than 300 monomer units in length.

In some embodiments, a number average molecular weight of the block copolymer ranges from 2000 Da or less to 500,000 Da or more. For example, a number average molecular weight of the block copolymer may range anywhere from 2000 Da to 5000 Da to 10,000 Da to 20,000 Da to 50,000 Da to 100,000 Da to 200,000 Da to 500,000 Da in number average molecular weight.

In some embodiments, the block copolymer is a triblock copolymer having a poly(2-(di-($C_{1-5}$)alkylamino)($C_{1-5}$)alkyl methacrylate) central block and two poly(N-isopropylamino acrylamide) outer blocks.

In some embodiments, the block copolymer is a triblock copolymer having a poly(N-isopropylamino acrylamide) central block and two poly(2-(di-($C_{1-5}$)alkylamino)($C_{1-5}$) alkyl methacrylate) outer blocks. Such a triblock copolymer, where the poly(2-(di-($C_{1-5}$)alkylamino)($C_{1-5}$)alkyl methacrylate) blocks are poly(2-(dibutylamino)ethyl methacrylate) blocks, is shown in FIG. 1, where l and n are integers. For example, l may an integer ranging from 10 to 500, and n may be an integer ranging from 5 to 1000.

Figure 2:
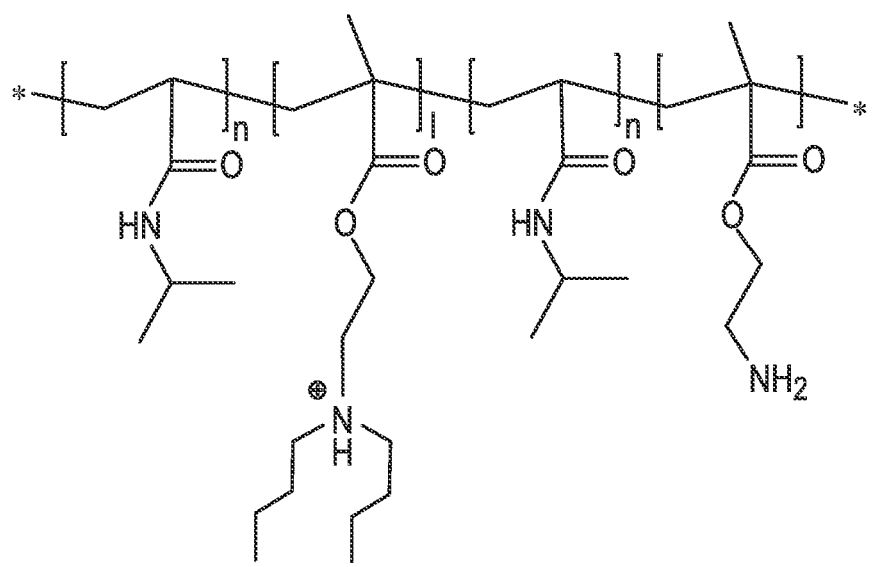
FIG. 2 is a schematic illustration of a NIPAAM-DBA-NIPAAM triblock copolymer with an additional amino group, in accordance with an embodiment of the present disclosure.

In some embodiments, the block copolymer further comprises an additional polymer block that comprises amine groups, which can be formed from amine-containing monomers. For example, the additional polymer block may comprise amine groups selected from aminoalkyl groups (e.g., amino-$C_1$-$C_4$-alkyl groups), alkylaminoalkyl groups (e.g., $C_1$-$C_4$-alkylamino-$C_1$-$C_4$-alkyl groups), or dialkylaminoalkyl groups (e.g., di-$C_1$-$C_4$-alkyl-amino-$C_1$-$C_4$-alkyl) groups), specific examples of which include aminomethyl, aminoethyl, aminopropyl, methylaminomethyl, dimethylaminomethyl, ethylaminomethyl, diethylaminomethyl, methylaminoethyl, dimethylaminoethyl, ethylaminoethyl, diethylaminoethyl, methylaminopropyl, dimethylaminopropyl, ethylaminopropyl or diethylaminopropyl groups. In some embodiments, the additional polymer block ranges from 1 to 500 or more monomer units in length, for example, ranging anywhere from 1 to 2 to 5 to 10 to 20 to 50 to 100 to 200 to 500 monomer units in length. An example of such a block copolymer is shown in FIG. 2, where the amine-containing monomer is 2-aminoethyl methacrylate. Such monomers can provide an additional functional group for later linkage with molecules, such as thrombin peptides, among other purposes. During the synthesis of the block copolymers by RAFT technique illustrated in FIG. 2, the amino group in 2-aminoethyl methacrylate may be protected to avoid interference with chain transfer agent by using common protection groups. Typical protection groups include 9-fluorenylmethyl carbamate, t-butyl carbamate, benzyl carbamate, acetamide, and trifluoroacetamide, among others. After polymerization, the protection group would be deprotected accordingly.

In some embodiments, the block copolymer is present in a concentration ranging from 1% wt/wt or less to 50% wt/wt or more with respect to the weight of the composition, which may be, for instance, a liquid composition such as an aqueous liquid composition. For example, the block copolymer may be present in the composition in a concentration ranging anywhere from 1% wt/wt to 2% wt/wt to 5% wt/wt to 10% wt/wt to 20% wt/wt to 30% wt/wt to 40% wt/wt to 50% wt/wt.

In some embodiments, the compositions of the present disclosure further comprise at least one anionic polymer that comprises one or more groups selected from sulfonate groups, sulfate groups, phosphate groups, phosphonate groups or carboxylate groups, which are negatively charged at pH 7, are preferably negatively charged at pH greater than 4 or 5, and in some cases are negatively charged at pH greater than 2. Such anionic polymers may be combined/mixed with the block copolymer to further tune the properties of the gel compositions described herein, including gel strength, softness, cohesiveness, fluidity, and/or gel stability, among other properties. Particular examples of anionic polymers include sulfonate polymers such as poly(2-acrylamido-2-methylpropane sulfonate) (polyAMPS) or polystyrene sulfonate, polyphosphates, poly(carboxylic acids) such as poly(acrylic acid) or poly(methacrylic acid), negatively charged polysaccharides including alginates, hyaluronates, pectin, carrageenan, gellan gum, gum arabic, guar gum or xanthan gum. The anionic polymer may be provided in a salt form, for example, in a sodium salt form or a potassium salt form, among others. In some embodiments, the anionic polymer may have a number average molecular weight ranging from 1,000 Da to 5,000,000 Da, for example ranging anywhere from 1,000 Da to 2,000 Da to 5,000 Da to 10,000 Da to 20,000 Da to 50,000 Da to 100,000 Da to 200,000 Da to 500,000 Da to 1,000,000 Da to 2,000,000 Da to 5,000,000 Da.

In some embodiments, the at least one anionic polymer is present in an amount ranging from 0.1% wt/wt or less to 50% wt/wt or more with respect to the weight of the composition, which may be, for instance, a liquid composition such as an aqueous liquid composition. For example, the at least one anionic polymer may range anywhere from 0.1% wt/wt to 0.2% wt/wt to 0.5% wt/wt to 1% wt/wt to 2% wt/wt to 5% wt/wt to 10% wt/wt to 20% wt/wt to 30% wt/wt to 40% wt/wt to 50% wt/wt with respect to the weight of the composition.

In some embodiments, a molar ratio of the positively charged amino groups in the DBA blocks (assuming 100% ionization) to the negatively charged groups in the anionic polymer (assuming 100% ionization) ranges from 0.1:1 to 10:1, typically 0.5:1 to 2:1, more typically 1:1 to 1:1.5.

In some embodiments, the compositions may further comprise at least one imaging agent. Examples of imaging agents include radiocontrast agents, imageable radioisotopes, fluorescent dyes, magnetic resonance imaging (MRI) contrast agents, ultrasound contrast agents and near-infrared (NIR) imaging contrast agents. Particular examples of radiocontrast agents include metallic particles such as particles of tantalum, tungsten, rhenium, niobium, molybdenum, and their alloys, which metallic particles may be spherical or non-spherical. Particular examples of radiocontrast agents further include non-ionic radiocontrast agents, such as iohexol, iodixanol, ioversol, iopamidol, ioxilan, or iopromide, ionic radiocontrast agents such as diatrizoate, iothalamate, metrizoate, or ioxaglate, and iodinated oils, including ethiodized poppyseed oil (available as Lipiodol®). Further particular examples of imaging agents include (a) fluorescent dyes such as fluorescein, indocyanine green, or fluorescent proteins (e.g. green, blue, cyan fluorescent proteins), (b) contrast agents for use in conjunction with magnetic resonance imaging (MRI), including contrast agents that contain elements that form paramagnetic ions, such as $Gd^{(III)}$, $Mn^{(II)}$, $Fe^{(III)}$ and compounds (including chelates) containing the same, such as gadolinium ion chelated with diethylenetriaminepentaacetic acid, (c) contrast agents for use in conjunction with ultrasound imaging, including organic and inorganic echogenic particles (i.e., particles that result in an increase in the reflected ultrasonic energy) or organic and inorganic echolucent particles (i.e., particles that result in a decrease in the reflected ultrasonic energy), (d) contrast agents for use in connection with near-infrared (NIR) imaging, which can be selected to impart near-infrared fluorescence to the hydrogels of the present disclosure, allowing for deep tissue imaging and device marking, for instance, NIR-sensitive nanoparticles such as gold nanoshells, carbon nanotubes (e.g., nanotubes derivatized with hydroxyl or carboxyl groups, for instance, partially oxidized carbon nanotubes), dye-containing nanoparticles, such as dye-doped nanofibers and dye-encapsulating nanoparticles, and semiconductor quantum dots, among others, and NIR-sensitive dyes such as cyanine dyes, squaraines, phthalocyanines, porphyrin derivatives and boron dipyrromethane (BODIPY) analogs, among others, and (e) imageable radioisotopes including $^{99m}$Tc, $^{201}$Th, $^{51}$Cr, $^{67}$Ga, $^{68}$Ga, $^{111}$In, $^{64}$Cu, $^{89}$Zr, $^{59}$Fe, $^{42}$K, $^{82}$Rb, $^{24}$Na, $^{45}$Ti, $^{44}$Sc, $^{51}$Cr and $^{177}$Lu, among others.

In some embodiments, the at least one imaging agent is present in an amount ranging from 1% wt/wt or less to 50% wt/wt or more with respect to the weight of the composition, which may be, for instance, a liquid composition such as an aqueous liquid composition. For example, the at least one imaging agent may be present in the composition in a concentration ranging anywhere from 1% wt/wt to 2% wt/wt to 5% wt/wt to 10% wt/wt to 20% wt/wt to 30% wt/wt to 40% wt/wt to 50% wt/wt.

In some embodiments, the compositions may further comprise one or more therapeutic agents. Examples of therapeutic agents include small molecule therapeutic agents (defined herein as therapeutic agents having a molecular weight less than 2000 g/mol, typically less than 1500 g/mol, more typically less than 1000 g/mol), biomolecules (e.g., polypeptides including proteins and protein fragments, such as antibodies and antibody fragments and oligopeptides, as well as polynucleotides and oligonucleotides, including nucleic acids and nucleic acid analogs such as deoxyribonucleic acids, ribonucleic acids, peptide nucleic acids, and fragments thereof), and radioisotopes.

In some embodiments, the one or more therapeutic agent is present in an amount ranging from 0.001% wt/wt (10 ppm) or less to 80% wt/wt or more with respect to the weight of the composition, which may be, for instance, a liquid composition such as an aqueous liquid composition. For example, the one or more therapeutic agents may be present in the composition in a concentration ranging anywhere from 0.001% wt/wt to 0.002% wt/wt to 0.005% wt/wt to 0.01% wt/wt to 0.02% wt/wt to 0.05% wt/wt to 0.1% wt/wt to 0.2% wt/wt to 0.5% wt/wt to 1% wt/wt to 2% wt/wt to 5% wt/wt to 10% wt/wt to 20% wt/wt to 50% wt/wt to 80% wt/wt.

Specific examples of therapeutic agents include antiangiogenic agents, cytotoxic agents, chemotherapeutic agents, checkpoint inhibitors, immune modulatory cytokines, T-cell agonists, and STING (stimulator of interferon genes) agonists, among others.

Examples of therapeutic agents include: checkpoint inhibitors including inhibitors of the binding of PD-1 to PD-L1, inhibitors of the binding of CTLA-4 to CD80 and/or CD86, inhibitors of the binding of TIGIT to CD-112, and inhibitors of the binding of LAG-3 to MHC class II molecules; antibodies or antigen binding fragments thereof that bind to PD-1 (e.g., pembrolizumab, nivolumab domvanalimab, etc.), PD-L1 (e.g., atezolizumab, avelumab, durvalumab, etc.), LAG-3 (e.g., relatlimab, etc.), TIM-3 (e.g., LY3321367, MBG453, TSR-022, etc.), TIGIT (e.g., etigilimab, tiragolumab, vibostolimab, etc.), or CTLA-4 (e.g., ipilimumab tremelimumab, etc.); antibodies or antigen binding fragments thereof that bind to CD3, CD19, CD20, CD22, CD52, CD79B, CD30, CD33, CD38, CD52, CD79B, HER2, EGFR, VEGF, VEGFR2, EPCAM/CD3, GD2, IL-6, RANKL, SLAMF7, CCR4, PDGFRα, Nectin-4 or TROP2; immune modulatory cytokines such as IL-2, IL-12, IL-15, IL-23, interferon gamma (IFN-γ) and gm-CSF (granulocyte macrophage colony stimulating factor); T-cell agonists such as TLR3 agonists (e.g., polyinosinic:polycytidylic acid, double stranded RNAs, etc.), TLR7 agonists (e.g., TMX-202, gardiquimod, imiquimod, etc.), TLR8 agonists (e.g., VTX-2337, etc.), TLR7/8 agonists (e.g., MEDI9197, R848, resiquimod, etc.), TLR9 agonists (e.g., lefitolimod (MGN1703), tilsotolimod, CpG oligodeoxynucleotides (e.g., agatolimod), etc.); and STING agonists such as GSK 532, cyclic dinucleotides (e.g., cyclic guanosine monophosphate-adenosine monophosphate), CRD5500 (LB-061), E7766, ADU-S100, SB11285 MSA2, MK1454, TTI-10001, etc.), among others.

Examples of therapeutic agents also include: camptothecins (such as irinotecan, topotecan and exatecan) and anthracyclines (such as doxorubicin, daunorubicin, idarubicin and epirubicin), antiangiogenic agents (such as vascular endothelial growth factor receptor (VEGFR) inhibitors, such as axitinib, bortezomib, bosutinib canertinib, dovitinib, dasatinib, erlotinib gefitinib, imatinib, lapatinib, lestaurtinib, masutinib, mubitinib, pazopanib, pazopanib semaxanib, sorafenib, sunitinib, tandutinib, vandetanib, vatalanib and vismodegib), microtubule assembly inhibitors (such as vinblastine, vinorelbine and vincristine), aromatase inhibitors (such as anastrazole), platinum drugs (such as cisplatin, oxaliplatin, carboplatin and miriplatin), nucleoside analogues (such as 5-FU, cytarabine, fludarabine and gemcitabine), paclitaxel, docetaxel, mitomycin C, mitoxantrone, bleomycin, pingyangmycin, abiraterone, amifostine, buserelin, degarelix, folinic acid, goserelin, lanreotide, lenalidomide, letrozole, leuprorelin, octreotide, tamoxifen, triptorelin, bendamustine, chlorambucil, dacarbazine, melphalan, procarbazine, temozolomide, rapamycin (and analogues, such as zotarolimus, everolimus, umirolimus and sirolimus), antimetabolites such as 5-fluorouracil, multityrosine kinase inhibitors such as sorafenib, sunitinib, regorafenib, brivanib, dasatinib, bosutinib, erlotinib, gefitinib, imatinib and vandetinib, methotrexate, pemetrexed, or raltitrexed.

Therapeutic radioisotopes include, but are not limited to, $^{177}$Lu, $^{90}$Y, $^{131}$I, $^{89}$Sr, $^{153}$Sm, $^{223}$Ra, $^{224}$Ra, $^{211}$At, $^{225}$Ac, $^{227}$Th, $^{212}$Bi, $^{213}$Bi, and/or $^{212}$Pb.

In some embodiments, the compositions described herein may comprise therapeutic agents that are charged and/or uncharged at physiological pH. The charged therapeutic agents may be electrostatically held within the gel compositions and subsequently released therefrom by an ion exchange mechanism (e.g., where the compositions further comprise an anionic polymer that comprises one or more negatively charged groups selected from sulfonate groups, sulfate groups, phosphate groups, phosphonate groups or carboxylate groups). Charged therapeutic agents electrostatically held in the gel compositions may elute from the gel compositions in electrolytic media, such as physiological saline (0.90% w/v NaCl) or in-vivo, e.g., in the blood or tissues, to provide a sustained release of therapeutic agent over several hours, days or even weeks. Uncharged therapeutic agents in the gel compositions may also elute from the gel compositions in vivo. This may be particularly advantageous, for example, when rapid elution or a "burst effect" is desired, for example, for rapid therapeutic agent delivery to tissue, or when the low solubility of the therapeutic agent under physiological conditions determines the release profile rather than ionic interaction.

Embodiments of the present disclosure also relate to medical compositions that correspond to, or are formed from, the liquid compositions of any of the preceding embodiments. For example, as previous noted, such liquid compositions can be used for the in vivo formation of embolizations, fiducial markers, tissue bulking materials, tissue-spacing materials, and therapeutic agent depots.

Embodiments of the present disclosure further relate to medical procedures that employ the liquid compositions described herein. For example, in some embodiments, the medical procedures are methods of tissue embolization that comprise delivering the liquid compositions into one or more blood vessels feeding the tissue. Such procedures may be used to treat a variety of conditions including treatment of arteriovenous malformations, treatment of gastrointestinal bleeding, treatment of endoleaks, filling of aneurysms, treatment of a bleed caused by disease or trauma, treatment of solid tumors, particularly hyper-vascular tumors, such as those of the liver, prostate, kidney, brain, colon, bone and lung, as well as benign hyperplastic conditions such as treatment of prostate hyperplasia or treatment of uterine fibroids.

In some embodiments, the medical procedures are methods of local or systemic therapeutic agent release that comprise delivering (e.g., by injecting, spraying, etc.) the liquid compositions described herein to a patient (e.g., onto tissue of the patient, into tissue of the patient, between tissues of the patient, etc.).

In some embodiments, the medical procedures are methods of treatment that comprise delivering (e.g., by injecting, spraying, etc.) the liquid compositions described herein into or onto a tumour of a patient, wherein the therapeutic agent is released into the tumour.

In some embodiments, the medical procedures are methods of spacing a first tissue from a second tissue that comprise delivering (e.g., injecting, etc.) the liquid compositions described herein between the first tissue and the second tissue (e.g., between prostate tissue and rectal tissue).

In some embodiments, the medical procedures are methods of treatment that comprise delivering (e.g., by injecting, spraying, etc.) the liquid compositions described herein into a patient as a fiducial marker.

In yet further embodiments, the present disclosure relates to the use of the liquid compositions described herein in the manufacture of a medicament for the treatment of various diseases and conditions, including treatment of arteriovenous malformations, treatment of gastrointestinal bleeding, filling of aneurysms, treatment of solid tumors, particularly hypervascular tumors, such as those of the liver, prostate, kidney, brain, colon, bone and lung, as well as treatment of benign hyperplastic conditions such as prostate hyperplasia or uterine fibroids.

The present disclosure also relates to the use of any of the therapeutic agents described herein in the manufacture of a medicament for the treatment of such diseases and conditions wherein the therapeutic agents is incorporated into a liquid or gel compositions described herein. The present disclosure also relates to the use of any of the therapeutic agents herein in the treatment of such diseases and conditions wherein the therapeutic agents is incorporated into a liquid or gel compositions described herein. The liquid compositions may be particularly used where the liquid compositions are delivered by the transcatheter route, by injecting, by implanting, by spraying, etc.

The preceding embodiments are directed to a block copolymer that contains one or more poly(N-isopropylamino acrylamide) blocks and one or more poly(2-(di-($C_{1-5}$)alkylamino)($C_{1-5}$)alkyl methacrylate) blocks. However, it should be understood that, in any of the embodiments described herein, any of the following blocks may be substituted for the one or more poly(2-(di-($C_{1-5}$)alkylamino)($C_{1-5}$)alkyl methacrylate) blocks: one or more poly(N,N-dimethylaminoethyl methacrylate) blocks, one or more poly(N,N-diethylaminoethyl methacrylate) blocks, one or more poly(2-(tetramethyleneimino)ethyl methacrylate) blocks, one or more poly(2-(pentamethyleneimino)ethyl methacrylate) blocks, one or more poly(2-(hexamethyleneimino)ethyl methacrylate) blocks, one or more poly(2-(piperidino)ethyl methacrylate)) blocks, one or more poly(dioctylaminoethyl acrylate) blocks, one or more poly(piperidylethyl acrylate) blocks, one or more poly(N,N-dimethylaminoethyl acrylate) blocks, one or more poly(N,N-diethylaminoethyl acrylate) blocks, one or more poly(N,N-diisopropylaminoethyl acrylate) blocks, one or more poly(N,N-di(n-butyl)-aminoethyl acrylate) blocks, one or more poly(2-(tetramethyleneimino)ethyl acrylate) blocks, one or more poly(2-(pentamethyleneimino)ethyl acrylate) blocks, one or more poly(2-(hexamethyleneimino)ethyl acrylate) blocks, one or more poly(N,N-dimethylaminoethyl methacrylamide) blocks, one or more poly(N,N-diethylaminoethyl methacrylamide) blocks, one or more poly(N,N-diisopropylaminoethyl methacrylamide) blocks, one or more poly(N,N-di(n-butyl)-aminoethyl methacrylamide) blocks, one or more poly(2-(tetramethyleneimino)ethyl methacrylamide) blocks, one or more poly (2-(pentamethyleneimino)ethyl methacrylamide) blocks, one or more poly(2-(hexamethyleneimino)ethyl methacrylamide) blocks, one or more poly(2-(piperidino)ethyl methacrylamide)) blocks, one or more poly(dioctylaminoethyl acrylamide) blocks, one or more poly(piperidylethyl acrylamide) blocks, one or more poly(N,N-dimethylaminoethyl acrylamide) blocks, one or more poly(N,N-diethylaminoethyl acrylamide) blocks, one or more poly(N,N-diisopropylaminoethyl acrylamide) blocks, one or more poly(N,N-di(n-butyl)-aminoethyl acrylamide) blocks, one or more poly(2-(tetramethyleneimino)ethyl acrylamide) blocks, one or more poly(2-(pentamethyleneimino)ethyl acrylamide) blocks, or one or more poly(2-(hexamethyleneimino)ethyl acrylamide) blocks, among others.

Experimental

Specific examples pertaining to ABA triblock copolymer compositions will now be set forth, in which the ABA triblock copolymer includes a pH responsive central poly(2-(dibutylamino)ethyl methacrylate) block and two thermal responsive poly(N-isopropylamino acrylamide) end blocks (see FIG. 1). The ABA triblock copolymer was synthesized by using RAFT (Reversible-Addition-Fragmentation Chain-Transfer Radical Polymerization) technique, which started with polymerisation of N-Isopropylacrylamide (NIPAAM) initiated by 4,4'-azobis(4-cyanovaleric acid) (ACVA) and chain transfer agent 4-((((2-Carboxyethyl)thio)carbonothioyl)thio)-4-cyanopentanoic acid (CETCPA). After the first block was synthesized, a DBA block was polymerized using protonated 2-(dibutylamino)ethyl methacrylate monomer (DBA), followed by copolymerization of third block of NIPAAM (see FIG. 4). Methanol was used as reaction solvent.

Without being bound by theory, it is believed that a solution of the resulting NIPAAM-DBA-NIPAAM copolymer forms a physically cross-linked hydrogel at physiological conditions, pH 7 and 37° C., through hydrophobic interactions. In this regard, at ambient temperature (20-25° C.) and pH 5-6, an aqueous solution of the resulting NIPAAM-DBA-NIPAAM copolymer is in a liquid form with free-flowing properties because both NIPAAM and DBA block are water soluble. When mixed with polyAMPS, positively charged amine groups of the DBA block form a complex with negatively charged sulfonate groups of the polyAMPS to create a coacervate viscous liquid phase (illustrated schematically in FIG. 3A). This viscous liquid is relatively easily deliverable through a 2.7-2.8 Fr catheter using a 1- or 3-mL syringe. During catheter delivery, the temperature of the blood vessel in which the catheter is located is around 37° C., so that the temperature of the complex liquid would increase to about 30-37° C. The sol-gel transition of NIPAAM blocks occurs due to the increased hydrophobicity of NIPAAM at the higher temperature, and a physically cross-linked "flowable" hydrogel structure comprised of mixed micelles and complexes is formed (illustrated schematically in FIG. 3B). The micellar core is NIPAAM and corona part is balanced by the hydrophilic and protonated DBA block which interacts with the polyAMPS. If this gel is then placed in a physiological solution at pH 7-7.4 (e.g., in the vasculature), partial DBA deprotonation occurs, as DBA has a pKa=5. The hydrogel structure is further enhanced by the increased hydrophobicity of the DBA block, and the hydrogel strength and viscosity are significantly increased (illustrated schematically in FIG. 3C).

EXAMPLE 1

Synthesis of pNIPAAM$_{300}$

Figure 5A:
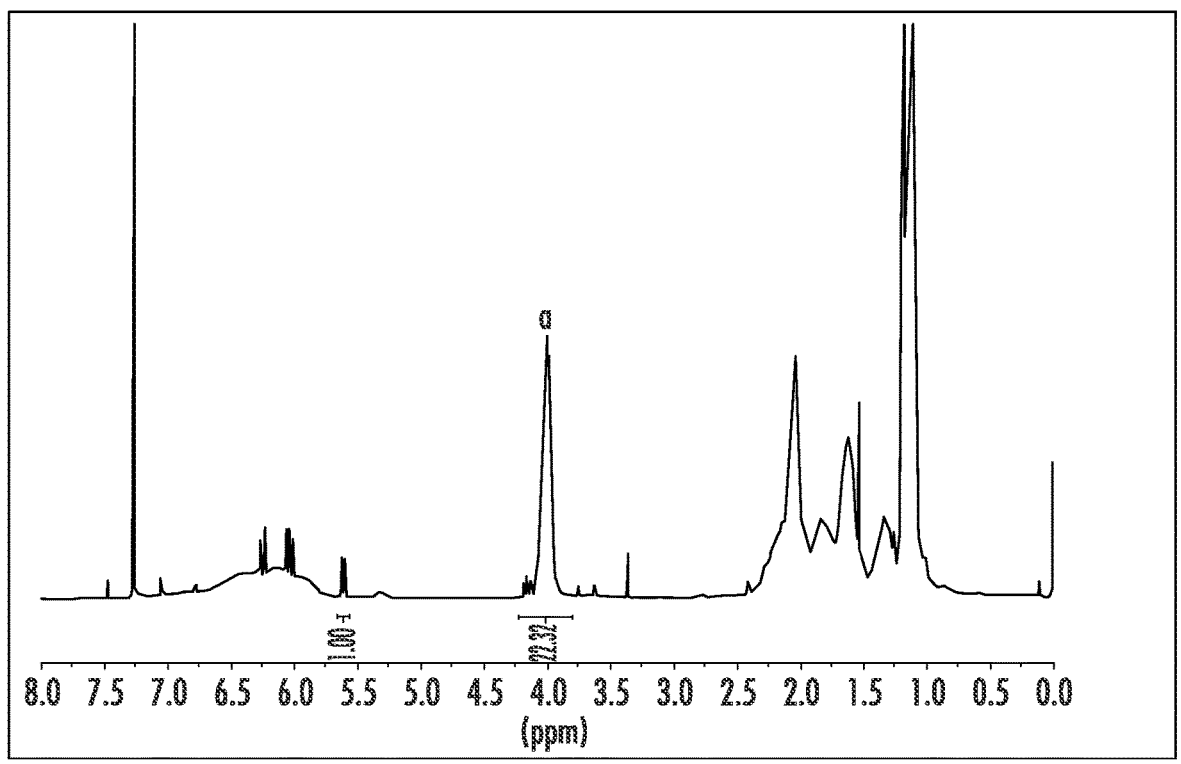
FIG. 5A is a proton NMR of a polymer after formation of an initial pNIPAAM block, in accordance with an embodiment of the present disclosure.

CETCPA (0.0272 g, 0.09 mmol), NIPAAM (3 g, 26.51 mmol, NIPAAM/CPATTC molar ratio=300) and ACVA (5 mg, 0.02 mmol, ACVA/CETCPA molar ratio=0.2) were added to a round bottomed flask (RBF) and dissolved with 3 mL of methanol. The RBF was sealed with a rubber stopper and the reaction mixture degassed with N$_2$ for a minimum of 30 min. The degassing step was carried out with a short needle (in the stopper, as outlet) and a long needle (as inlet) with N$_2$ bubbling directly in the reaction mixture whilst maintaining the RBF in an ice bath under constant stirring. After degassing, the RBF was placed in a preheated oil bath at 70° C. and the reaction left to proceed for 24 hours under constant magnetic stirring. The reaction was stopped by opening the RBF to air and placing the RBF in an ice bath. An aliquot of the reaction mixture (50 µL) was withdrawn for $^1$H NMR analysis (see FIG. 5A). No purification was carried out. The proton NMR analysis of the mixture showed that over 98% of the NIPAAM monomer has reacted.

EXAMPLE 2

Figure 5B:
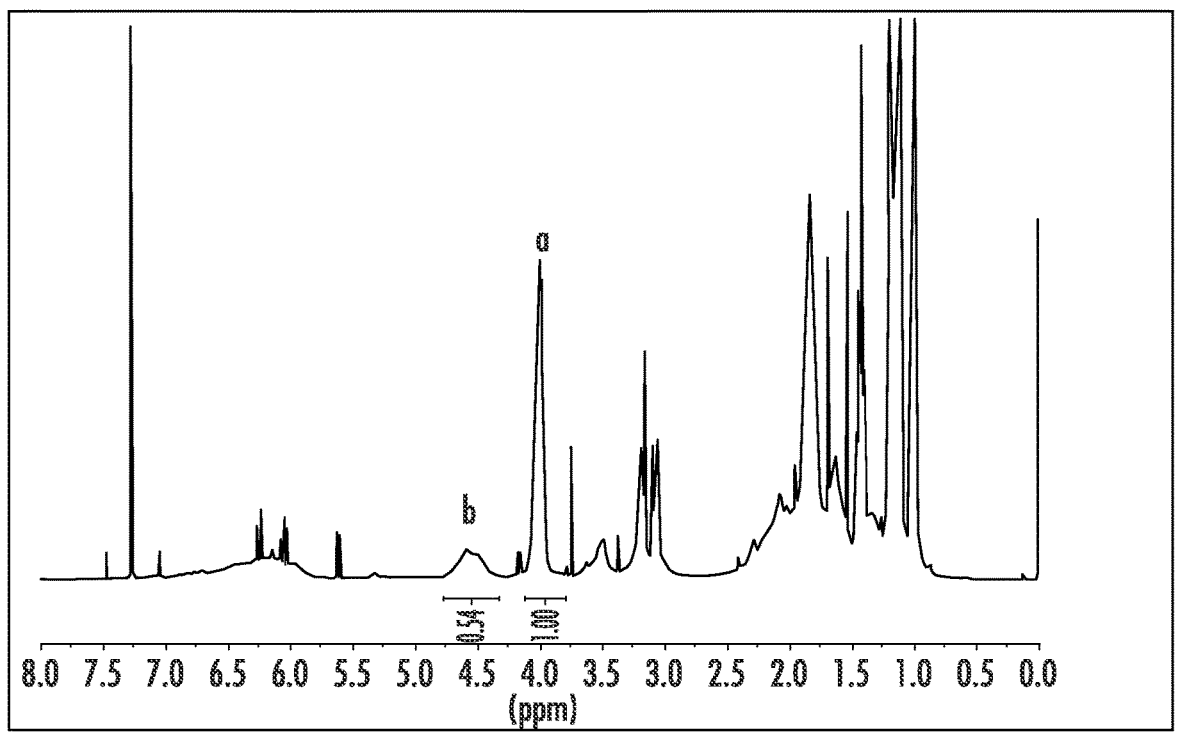
FIG. 5B is a proton NMR of a polymer after formation of a pNIPAAM-b-pDBA diblock copolymer, in accordance with an embodiment of the present disclosure.

Synthesis of pNIPAAM$_{300}$-pDBA$_{100}$ 2-(Dibutylamino)ethyl methacrylate (DBA) (2.13 g, 8.84 mmol, DBA/pNIPAAM$_{300}$ molar ratio=100) and deionized water (2 mL) were mixed in an RBF and stirred with a magnetic stirrer. The RBF was placed in an ice bath while adding HCl 25 wt. % solution (1.151 mL, DBA/HCl molar ratio=1) and kept at room temperature under constant stirring until all DBA dissolved. The pH of the mixture was adjusted to 6 with a NaOH 1M solution (0.673 mL). The protonated DBA solution was transferred into the RBF containing pNIPAAM$_{300}$ prepared in the previous step. ACVA (5 mg, 0.02 mmol, ACVA/pNIPAAM$_{300}$ molar ratio=0.2) was then added to the reaction mixture. Similarly, the reaction mixture was degassed with N$_2$ for 30 min before placing the RBF in a preheated oil bath at 70° C. for 24 hours. An aliquot of the reaction mixture (50 µL) was withdrawn for $^1$H NMR analysis (see FIG. 5B). No purification was carried out.

EXAMPLE 3

Synthesis of pNIPAAM$_{300}$-pDBA$_{100}$-pNIPAAM$_{300}$

Figure 4:
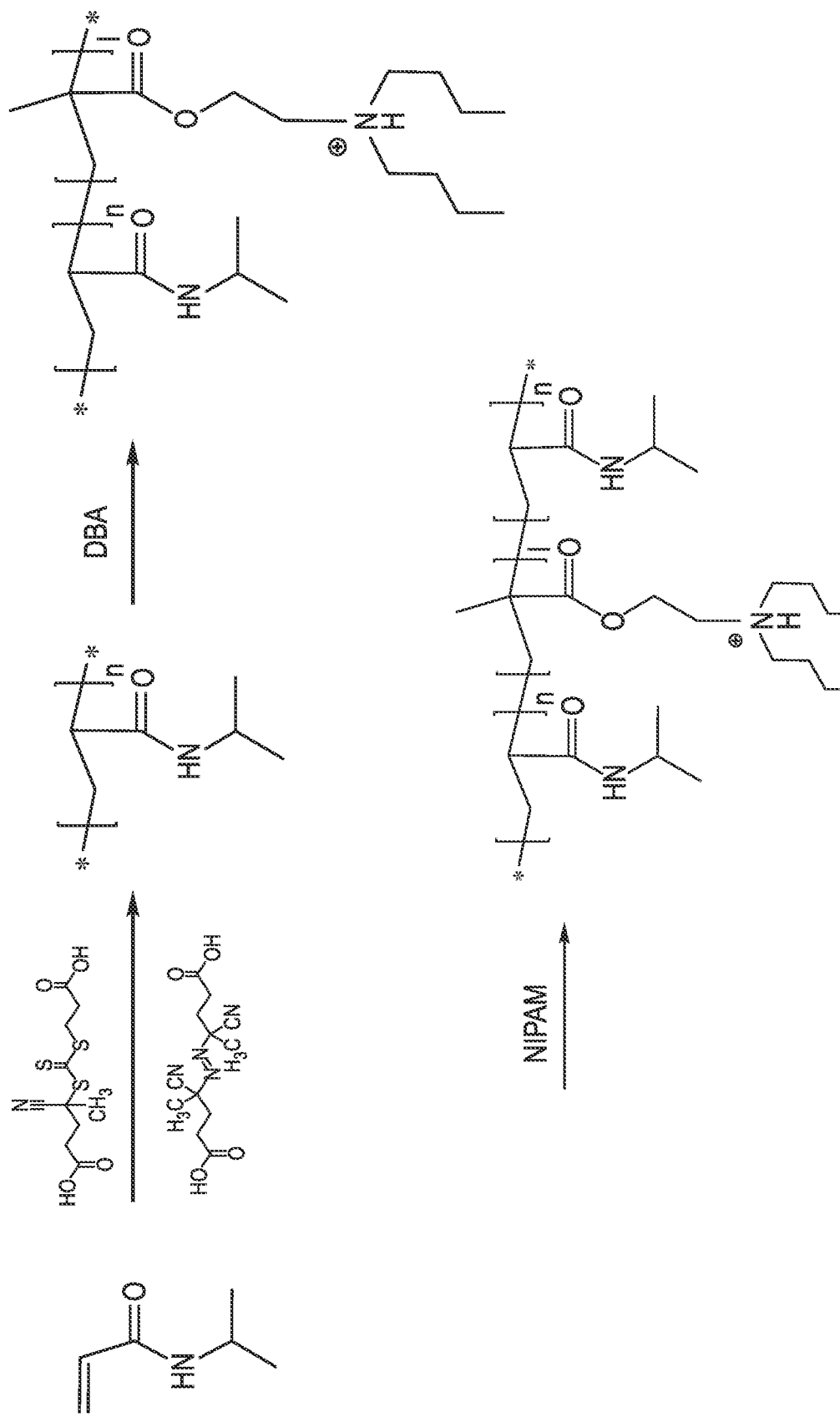
FIG. 4 is a schematic illustration of the synthesis of a pNIPAAM-b-pDBA-b-pNIPAAM triblock copolymer in accordance with an embodiment of the present disclosure.
Figure 5C:
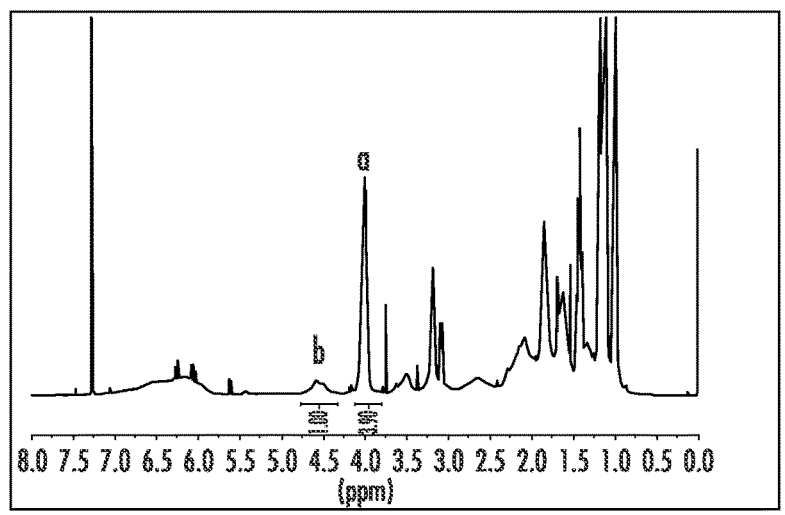
FIG. 5C is a proton NMR of a polymer after formation of a pNIPAAM-b-pDBA-b-pNIPAAMa triblock copolymer, in accordance with an embodiment of the present disclosure.
Figure 5D:
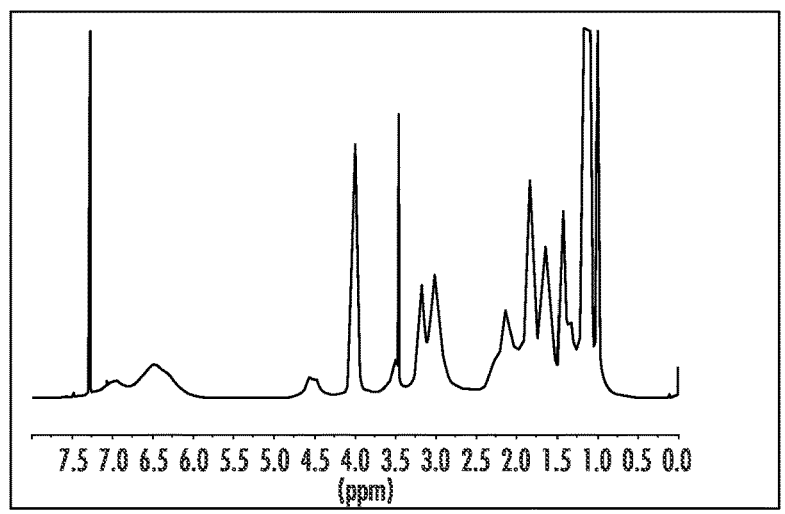
FIG. 5D is a proton NMR of a pNIPAAM-b-pDBA-b-pNIPAAMa triblock copolymer after purification by dialysis against methanol (dialysis membrane MWCO 12000-14000 Da) in accordance with an embodiment of the present disclosure.

In the RBF containing pNIPAAM$_{300}$-pDBA$_{100}$, NIPAAM (3 g, 26.51 mmol, NIPAAM/pNIPAAM$_{300}$-pDBA$_{100}$ molar ratio=300) was added with ACVA (5 mg, 0.02 mmol, ACVA/pNIPAAM$_{300}$-pDBA$_{100}$ molar ratio=0.2) and methanol (4 mL). The reaction mixture was degassed with N$_2$ for a minimum of 30 min before placing the RBF in a preheated oil bath at 70° C. for 24 hours. An aliquot of the reaction mixture (50 µL) was withdrawn for $^1$H NMR analysis (see FIG. 5C). Dialysis purification was then performed, and the purified sample analysed by $^1$H NMR analysis (see FIG. 5D). The synthesis of the triblock copolymer is schematically illustrated in FIG. 4. A list of copolymers synthesized using this technique is shown in Table 1.

TABLE 1

| Sample | Target copolymer composition | Structure | Property |
|---|---|---|---|
| 1 | NIPAAM50-DBA25-NIPAAM50 | ABA | Thermal/pH responsive |
| 2 | NIPAAM100-DBA50-NIPAAM100 | ABA | Thermal/pH responsive |
| 3 | NIPAAM200-DBA100-NIPAAM200 | ABA | Thermal/pH responsive |
| 4 | NIPAAM300-DBA100-NIPAAM300 | ABA | Thermal/pH responsive |
| 5 | NIPAAM400-AMPS50-NIPAAM400 | ABA | Thermal responsive |
| 6 | NIPAAM300-DBA200-NIPAAM300 | ABA | Thermal/pH responsive |
| 7 | NIPAAM400-DBA200-NIPAAM400 | ABA | Thermal/pH responsive |
| 8 | NIPAAM200-DBA300-NIPAAM200 | ABA | Thermal/pH responsive |
| 9 | NIPAAM200-DBA400-NIPAAM200 | ABA | Thermal/pH responsive |
| 10 | NIPAAM300-(DBA100-co-AMPS30)-NIPAAM300 | ABA | Thermal/pH responsive |
| 11 | DBA200-NIPAAM300-DBA200 | BAB | Thermal/pH responsive |
| 12 | NIPAAM300-DEA100-NIPAAM300 | ABA | Thermal/pH responsive |
| 13 | NIPAAM10-DBA50-NIPAAM10 | ABA | Thermal/pH responsive |
| 14 | NIPAAM10-DBA100-NIPAAM10 | ABA | Thermal/pH responsive |
| 15 | NIPAAM10-DBA150-NIPAAM10 | ABA | Thermal/pH responsive |

EXAMPLE 4

Synthesis NIPAAM-DEA-NIPAAM Triblock Copolymer

The triblock copolymer was synthesized by the ATRP method. Diethyl meso-2,5-dibromoadipate 0.11 g (1 eq) initiator, DEA (2-(diethylamino)ethyl methacrylate) monomer 5.6 g (100 eq), HMTETA (1,1,4,7,10,10-hexamethyltriethylenetetramine) catalyst 0.138 g (2 eq), and copper (I) bromide 0.086 g (2 eq) were charged into a 250 mL three neck round bottom flask with 6 mL of anhydrous methanol. The mixture in flask was frozen by liquid nitrogen and degassed through three freeze-thaw processes, followed by polymerization in a 70° C. oil bath for overnight. The obtained DEA polymer was purified by passing through a silica gel column to remove copper catalyst. The polyDEA was further vacuum dried for 24 hours at 40° C.

2.5 g of obtained polyDEA macromer was mixed with NIPAAM monomer 6.0 g in 15 mL of anhydrous methanol, followed by nitrogen degas 50 min. Under nitrogen atmosphere, catalyst copper (I) bromide 0.038 g (2 eq) and Me$_4$Cyclam (1,4,8,11-tetramethyl-1,4,8,11-tetraazacyclotetradecane) 0.068 g (2 eq) were added at ambient temperature. The reaction was stirred overnight under nitrogen, and after the reaction completed, the solution was passed through a silica gel column to remove catalyst using MeOH as eluent. The solvent was removed by rotary evaporation, and the polymer was further dried under vacuum 40° C. for 24 hours.

EXAMPLE 5

Typical Procedure for Formulation of Polymeric Embolics by Mixing Triblock Copolymers and PolyAMPS As a typical procedure of preparation of complex hydrogel, to make a 20% wt/wt polymer solution, 2 g of triblock copolymer (Sample 4, Table 1) were dissolved in 8 g deionized water by repeatedly placing the vial of solution in either ice-water bath or in refrigerator (2-8° C.) for 1-2 hours, followed by roller mixing for 1 hour, until most of the solid polymer dissolved. The solution was then kept in a refrigerator overnight and again roller-mixed for 2 hours; a homogeneous solution was received.

Figure 6:
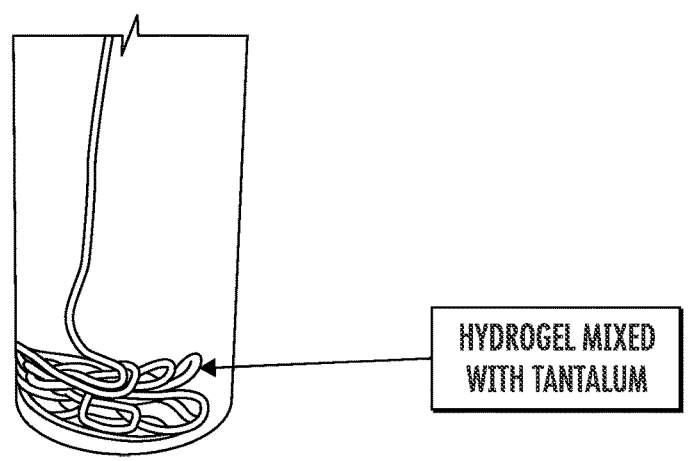
FIG. 6 is an image of hydrogel formation after delivery into 37° C. PBS (phosphate buffered saline), in accordance with an embodiment of the present disclosure.

The solution was mixed with 0.9 g of tantalum powder (20% solid content) uniformly in a 10 mL syringe. Air bubbles were removed by gently tapping the syringe. PolyAMPS sodium form was prepared by slowly adding NaOH powder to poly(2-acrylamido-2-methyl-1-propanesulfonic acid) solution (MW~2 million Da, 15% concentration) with stirring to adjust pH to around pH 4. To provide a charge ratio of around 1:1.5, 0.54 g polyAMPS in a second 10 mL syringe was mixed with the tantalum polymer suspension through a 3-way stopcock to form a uniform mixture. Then the mixture was pushed into one 10 mL syringe and capped for steam sterilization at 121° C., 30 min. The suspension was repeatedly mixed by exchange with another syringe through a 3-way stopcock at room temperature. Finally, the suspension was dispensed into a 1 mL syringe for catheter delivery. The final composition contained 11.1% wt/wt of the triblock copolymer, 3.7% wt/wt of the polyAMPS, and 20% wt/wt of the tantalum. FIG. 6 shows the hydrogel that was formed after injecting the composition through an 18 G needle into PBS buffer at 37° C. The PBS buffer composition is 140 mM NaCl, 10 mM phosphate buffer, and 3 mM KCl, pH 7.4.

A similar process was used to make a representative complex gel of NIPAAM-DEA-NIPAAM triblock copolymer and polyAMPS.

EXAMPLE 6

Rheology Study of Complex Gel with Different Charge Ratio Between DBA Block and PolyAMPS NIPAAM-DBA-NIPAAM copolymer solutions were prepared under slightly acidic conditions to allow the DBA block to be fully protonated, and the pH of the resulting solutions were measured to be around pH 5-6 range. When polyAMPS solution was mixed with the copolymer solutions through two syringe mixing, viscous coacervate solutions were formed at room temperature. By controlling the ratio between the charges of DBA and polyAMPS in the composition, the rheology properties of the solution could be varied.

Figure 7:
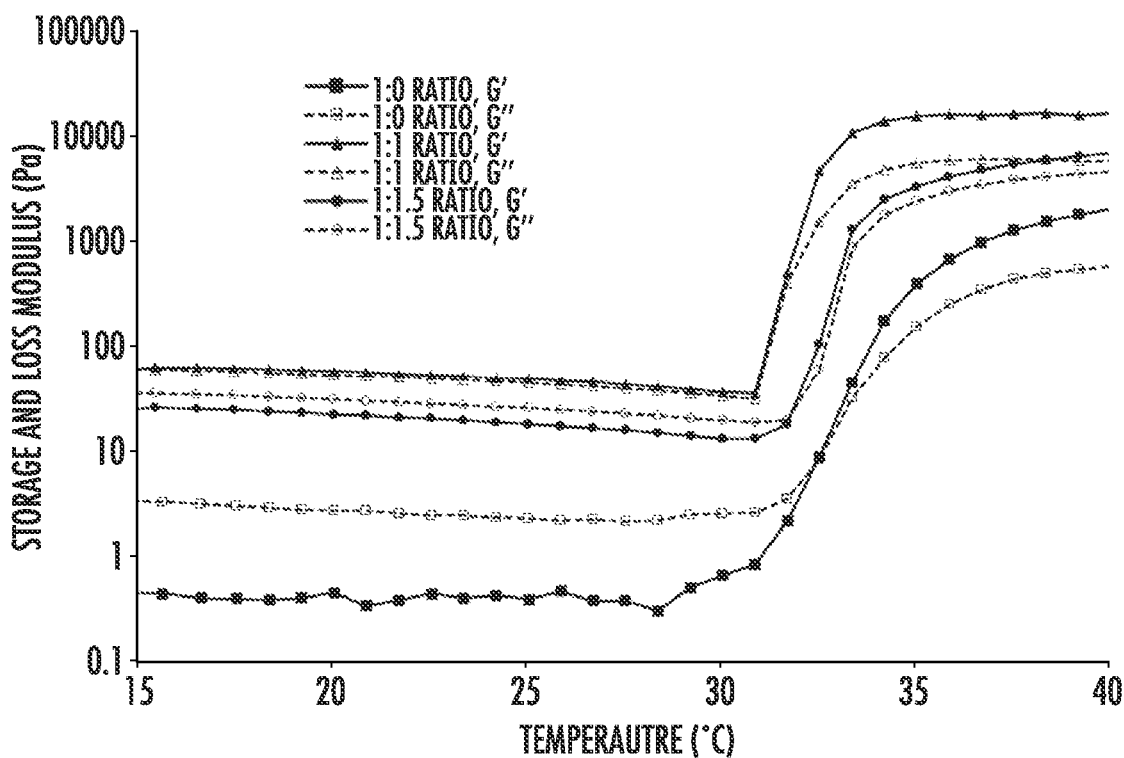
FIG. 7 is an illustration of storage and loss modulus versus temperature for several charge ratios between the pDBA block of pNIPAAM-b-pDBA-b-pNIPAAMa triblock copolymer and polyAMPS on the rheology properties of polymer complex, in accordance with embodiments of the present disclosure. The solid symbol is storage modulus (G'), and open symbol is loss modulus (G").

FIG. 7 shows rheology behaviors of NIPAAM300-DBA100-NIPAAM300 complex gels with different charge ratios, specifically, 1:0, 1:1 and 1:1.5, between DBA and polyAMPS. No tantalum powder was used in the test. FIG. 7 shows that without AMPS addition (1:0 ratio), there is no charge-charge interaction and the result is soft gel formation. In solution at low temperature (<30° C.), the hydrogels of copolymers with 1:1.5 ratio were relatively soft, behaving more like a soft solid (G'<100 Pa), compared to the 1:1 ratio gel which is a slightly harder gel. This may be due to the contribution of extra polyAMPS chain to lower both the storage and loss modulus. At elevated temperature around 37° C., all gels were more solid-like (G'>G"), and 1:1 ratio gels are harder compared to 1:1.5 ratio gels. For samples containing NIPAAM400-DBA200-NIPAAM400, the gels of 1:1 and 1:1.5 ratio showed almost the same behavior, which may be explained by high molecular weight and strong chain entanglement.

EXAMPLE 7

Figure 8:
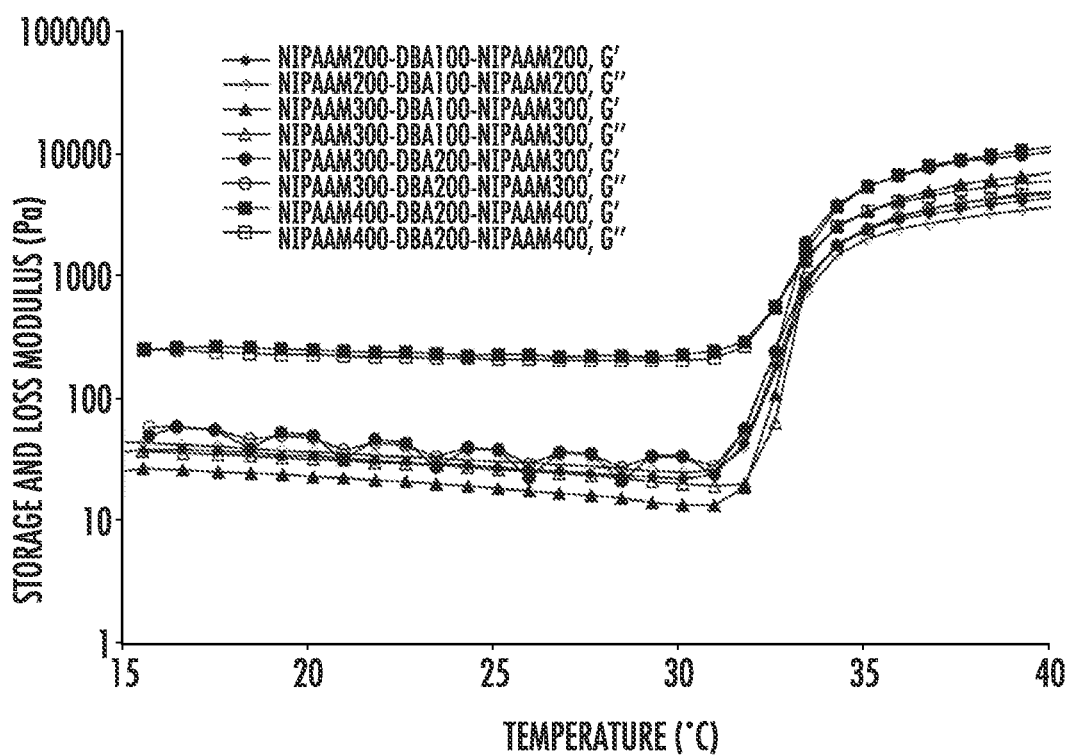
FIG. 8 is an illustration of storage modulus and loss modulus of various pNIPAAM-b-pDBA-b-pNIPAAMa triblock copolymers samples against temperature ramp, in accordance with embodiments of the present disclosure. The solid symbol is storage modulus (G'), and open symbol is loss modulus (G").

Effect of DBA and NIPAAM Chain on Rheology Properties of Temperature and pH Responsive Complex Gel FIG. 8, shows storage modulus and loss modulus of various pNIPAAM-b-pDBA-b-pNIPAAMa triblock copolymer samples against a temperature ramp. The results suggest that an increase in chain length of the NIPAAM block tends to increase the storage modulus of hydrogel at elevated temperature of around 37° C. No tantalum powder was used in the tests. When temperature was above 33-37° C., the storage modulus of DBA100 copolymer gel increased from 4 kPa to 7 kPa with a change from NIPAAM200 to NIPAAM300, respectively. The storage modulus of DBA200 copolymer gel increased from about 10 kPa to 11 kPa with a change from NIPAAM300 to NIPAAM400, respectively.

As seen from the graphs of FIG. 8, at temperature below 30° C., a complex gel of short chain copolymer behaved in a more liquid like manner, and the loss modulus was larger than storage modulus (from 10-50 Pa). With increased molecular weight to (Sample 7, Table 1), storage and loss modulus are almost the same, between 200-300 Pa, suggesting a more solid like complex gel. The measurement is consistent with the observation that sample 3 and 4 (Table 1) were relatively easy to deliver, and sample 6 and 7 (Table 1) were much harder gel with more force required for catheter delivery.

Without wishing to be bound by any theory, it appears that the role played by the DBA block in the formation of the hydrogel is complex with the DBA component interacting with polyAMPS at pH below pH 7 whilst the hydrophobic part enhances gel strength together with NIPAAM at 37° C. and pH 7. FIG. 8 shows two copolymers of DBA100 and DBA200 with the same NIPAAM300 length. The DBA200 copolymer has an increased storage modulus compared to the DBA100

To study the effect of DBA length, copolymers with DBA300 and DBA400 were synthesized and relevant complex hydrogel samples were prepared. Table 2 lists the morphology and property of the samples. Samples 4 and 6 (Table 2) both have a NIPAAM300 block with a DBA block of either 100 or 200 units; sample 3, 8 and 9 have a NIPAAM200 block with a DBA block of from 100-400 units. In general, the gel samples with short DBA chains of between 100-200 units are more homogenous and liquid like. The gels are relatively easier to be delivered through 2.7-2.8 Fr catheters.

TABLE 2

| Sample | Target copolymer composition | Gel morphology | Catheter deliverability and gel property |
|---|---|---|---|
| 1 | NIPAAM50-DBA25-NIPAAM50 | Aggregation/phase separation, broken gel lumps | Deliverable, very weak gel |
| 2 | NIPAAM100-DBA50-NIPAAM100 | Uniform mixture | Deliverable, weak gel |
| 4 | NIPAAM300-DBA100-NIPAAM300 | Uniform mixture | Deliverable, cohesive gel |
| 6 | NIPAAM300-DBA200-NIPAAM300 | Uniform mixture | Deliverable, cohesive gel |
| 7 | NIPAAM400-DBA200-NIPAAM400 | Uniform mixture | Deliverable, cohesive gel |
| 8 | NIPAAM200-DBA300-NIPAAM200 | Aggregation/phase separation, broken gel lumps | Hard solid precipitates caused syringe and catheter blockage, not deliverable |
| 9 | NIPAAM200-DBA400-NIPAAM200 | Aggregation/phase separation, broken gel lumps | Hard solid precipitates caused syringe and catheter blockage, not deliverable |
| 12 | NIPAAM200-DEA100-NIPAAM200 | Uniform gel mixture | Deliverable, weak gel |
| 13 | NIPAAM10-DBA50-NIPAAM10 | Uniform gel mixture with 1.0M NaCl | Deliverable, weak gel with fragments |
| 14 | NIPAAM10-DBA100-NIPAAM10 | Uniform gel mixture with 1.0M NaCl | Deliverable, cohesive gel |
| 15 | NIPAAM10-DBA150-NIPAAM10 | Uniform gel mixture with 1.0M NaCl | Deliverable, cohesive gel |

The samples with longer DBA units, i.e., 300-400 units, formed complex precipitates immediately when mixed with polyAMPS. It was found that complex gels were hard to mix, and this was true even at the sample preparation stage. The gels tended to break into small particles which then tended to aggregate resulting in blockages in the syringe. Because it was not possible to create a uniform gel, no rheology studies were carried out with the NIPAAM400-DBA300-NIPAAM400 mixed with polyAMPS

EXAMPLE 8

Effect of pH Change on Complex Gel Property

The complex hydrogels in this example are composed of protonated NIPAAM-DBA-NIPAAM triblock copolymer and polyAMPS in their pre- and post-delivery state with a pH range of 5-6. After delivery to the physiological environment, the DBA block starts to be partially deprotonated and becomes hydrophobic, which further enhanced the hydrophobicity of the complex gel with NIPAAM together at 37° C. Preliminary rheology studies were carried out by the oscillation method to measure the gel modulus. Initial studies were carried out on the gel at 37° C., followed by the addition of PBS buffer to the test cell to understand the effect of pH change on the gel properties. The cell was made of a 3D-printed plastic cylinder with an O-ring sealed at the bottom part connected to the test plate of the rheometer. The gel was first placed under a 25 mm parallel plate geometry for the oscillating test in air to study the gel behavior at pH 5-6, which mimics the gel pre-delivery within a catheter. Then pH 7.4 PBS buffer was added to the cell to cause a gel pH change, which mimics the gel post-delivery to a physiological environment. The changes of storage and loss modulus were recorded to demonstrate the gel behavior pre- and post-delivery.

Figure 9:
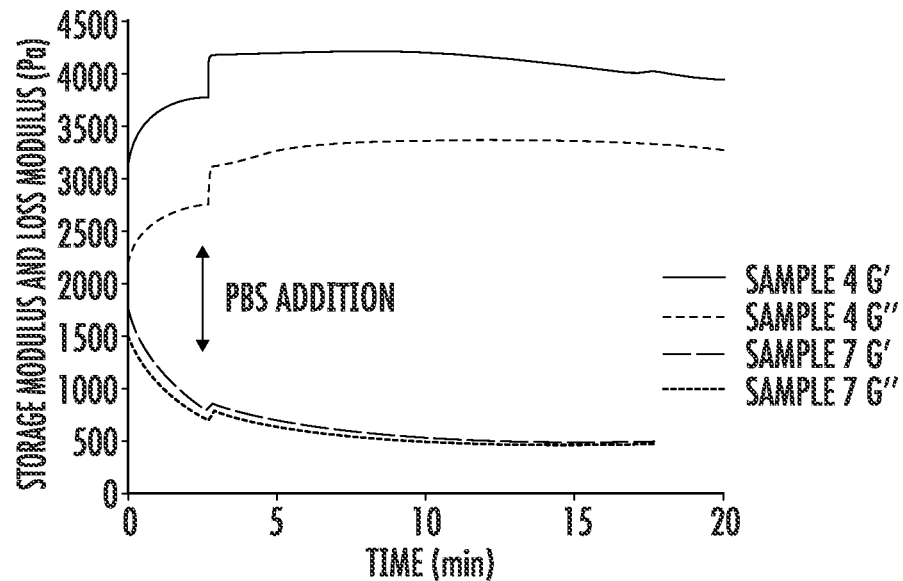
FIG. 9 shows modulus change introduced by adding PBS and by a pH increase, in accordance with an embodiment of the present disclosure.

FIG. 9 showed the test results of two complex gels of copolymer samples, NIPAAM300-DBA100-NIPAAM300 (Sample 4, Table 2) and NIPAAM400-DBA200-NIPAAM400 (Sample 7, Table 2) with polyAMPS in charge ratio of 1:1.5. The increase of modulus shown in FIG. 9 demonstrated that the deprotonation of the DBA moiety could enhance the hydrophobic interaction of the hydrogel network formed at elevated temperature. After PBS buffer was added, the increase in modulus observed in both samples was relatively small, possibly because the contact between the gel and the PBS solution was only occurring at the edge of the geometry initially; deprotonation of the internal gel might require a longer time period. It could also be that the higher fraction of NIPAAM in the polymer formed a more hydrophobic barrier that slowed down the PBS diffusion into the sample disc under the plate. Hence the observed modulus increase is much lower than the actual gel hardening in vivo would be, attributed to the very small contact area of the sample disc edge The rheology studies confirmed the thermal responsive nature of the polymer by increasing temperature from 15 to 40° C., and sol-gel transition of polymer solutions observed at about 32-34° C. These were measured at fixed shear strain of 0.1% and angular frequency 10 rad/s. The pH effect on the modulus of the hydrogel was studied by adding PBS on top of the polymer solution which was captured under a 25 mm flat geometry at 37° C. The same shear strain and angular frequency were applied.

EXAMPLE 9

Comparison Between NIPAAM-DEA-NIPAAM and NIPAAM-DBA-NIPAAM Triblock Copolymers

Figure 10:
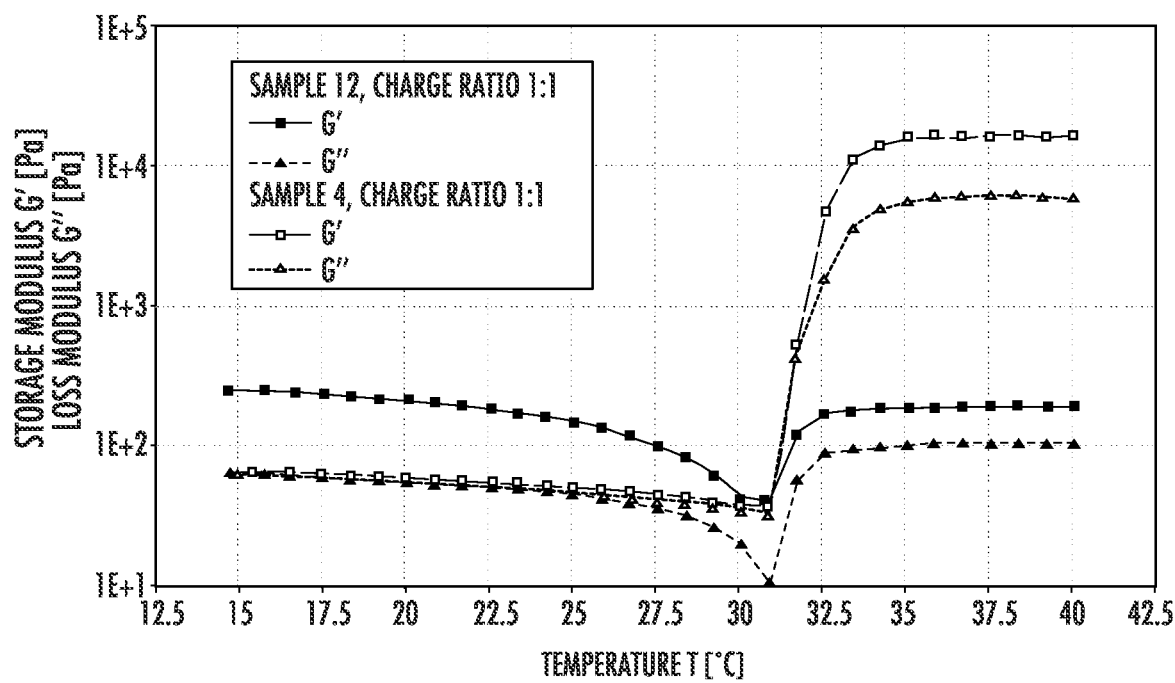
FIG. 10 shows modulus changes of NIPAAM-DEA-NIPAAM/polyAMPS complex gels (solid symbols) and NIPAAM-DBA-NIPAAM/polyAMPS complex gels (open symbols), in accordance with embodiments of the present disclosure. The square symbols denote storage modulus (G') and triangular symbols denote loss modulus (G").

Compared to triblock copolymer NIPAAM200-DBA100-NIPAAM200, the DEA block of NIPAAM200-DEA100-NIPAAM200 is less hydrophobic because of the four carbon difference between the diethylamino group vs. the dibutylamino group. FIG. 10 shows the impact of this difference on the rheology of the complex gel formed with polyAMPS. The complex gel of NIPAAM-DEA-NIPAAM was more solid-like, G'>G". Although it is temperature sensitive, its storage modulus at temperature around 37° C. (G'~200 Pa) was not significantly increased compared to that at 25° C., which suggested a weak gel. A visual check of the gel also indicated a uniform mixture and complexation between DEA block and polyAMPS (Table 2). Precipitation testing and flow model testing confirmed the rheology test data, i.e., gel fragment formation during agitation and passage through the pores of the flow model. In addition, the DEA block has pKa of 7.4 which suggests that the NIPAAM-DEA-NIPAAM copolymer would not show notable pH responsive property under physiological conditions.

EXAMPLE 11

Precipitation Test of Tantalum-Mixed Complex Gel with Different Compositions

Samples of the copolymer-polyAMPS complex gel mixed with 20% tantalum powder were first tested in PBS at 37° C.

by delivering the solution through a needle (18 Gage) into PBS and observing the precipitation. Sample 3, Sample 4, Sample 6 and Sample 7 were tested with two levels of polyAMPS in charge ratios 1:1 or 1:1.5. The compositions contained 9.2-12.9% wt/wt of the triblock copolymer, 2.4-4.0% wt/wt (1:1 ratio) or 3.2-5.1% wt/wt (1:1.5 ratio) of the polyAMPS, and 20% wt/wt of the tantalum. The test results were shown in Table 3. Sample 13, 14 and 15 were formulated with pAMPS in charge ratios 1:1, 1:1.2, 1:1.5 and 1:2. Tantalum powder and 1.0-1.2 M NaCl solution were added into the formulation as well. The compositions tested contained 5.0-7.3% wt/wt of the triblock copolymer, 5.0-7.7% wt/wt of the polyAMPS, and 20% wt/wt of the tantalum powder. The addition of NaCl is to shield the charge-charge interaction and to allow more distal delivery of the formulation. With the diffusion of concentrated NaCl from the fluid, the coacervated gel solidified and embolized narrow blood vessel.

TABLE 3

| Sample | Observed behavior |
| --- | --- |
| Sample 3/pAMPS (charge ratio 1:1) | Uniform gel, good gel strength |
| Sample 3/pAMPS (charge ratio 1:1.5) | Uniform gel, better gel strength than sample 3 1:1. |
| Sample 4/pAMPS (charge ratio 1:1) | Smooth gel, good gel strength. |
| Sample 4/pAMPS (charge ratio 1:1.5) | Smooth and uniform gel, good gel strength, slightly softer compared to sample 4 1:1. |
| Sample 6/pAMPS (charge ratio 1:1) | Fragments observed, weak gel strength. |
| Sample 6/pAMPS (charge ratio 1:1.5) | Large fragments observed, better gel strength than sample 6 1:1. |
| Sample 7/pAMPS (charge ratio 1:1) | Gel fragments and particles observed, rough surface, weak gel. |
| Sample 7/pAMPS (charge ratio 1:1.5) | Better gel than sample 7 1:1, smooth gel surface, more uniform gel. |
| Sample 13/pAMPS (charge ratio 1:1, 5.5% copolymer, 1.0M NaCl) | Fragmented and weak gel, large amount of free tantalum powder observed |
| Sample 13/pAMPS (charge ratio 1:1, 7.3% polymer, 1.0M NaCl) | Fragmented and weak gel, free tantalum powder observed |
| Sample 14/pAMPS (charge ratio 1:1, 6.4% copolymer, 1.0M NaCl) | Smooth gel with good gel strength |
| Sample 15/pAMPS (charge ratio 1:1, 6.3% copolymer, 1.0M NaCl) | Smooth and uniform gel with good gel strength |
| Sample 15/pAMPS (charge ratio 1:1.2, 5.8% copolymer, 1.0M NaCl) | Smooth and uniform gel with good gel strength |
| Sample 15/pAMPS (charge ratio 1:2, 5.7% copolymer, 1.0M NaCl) | Smooth and uniform gel. Softer and more fluid-like gel compared to sample 15 1:1.2 |

All eight samples were thread-like in gel form, which suggested that the gels were already beginning to form in the needle before delivery. Sample 3 and Sample 4 showed more cohesiveness with fewer gel particles/fragments in PBS. Sample 4 appeared to have an improved cohesiveness compared with sample 3. In addition, the gels with higher polyAMPS (1:1.5 ratio) were softer compared to the sample with 1:1 ratio, which is consistent with other rheology test results. The samples withstood strong vial-shaking at temperature around 37° C., and no broken fragments were observed. When the temperature of the PBS was dropped below 30° C., the gel started falling apart and tantalum powder leached out from the gel. Meanwhile, the solution became translucent which may be due to dispersed micelle formation from NIPAAM-DBA-NIPAAM block copolymers.

Samples 6 and 7 with longer DBA and NIPAAM chains appeared less cohesive when delivered into PBS buffer at 37° C., and large fragments of polymer and a small amount of tantalum powder were seen in solution even at temperature above 35° C. Similar to Samples 3 and 4, the gel with longer DBA and NIPAAM chains results in the formation of smaller fragments and dispersed tantalum powder, when temperature of PBS dropped below 30° C.

Based on the test results, Sample 4 had higher gel strength and cohesiveness even after vigorously shaking the vials, although it had 6 kPa storage modulus which suggested a relatively rigid gel.

EXAMPLE 12

Tantalum-Mixed Complex Gel Delivered in a Flow Model

Figure 11:
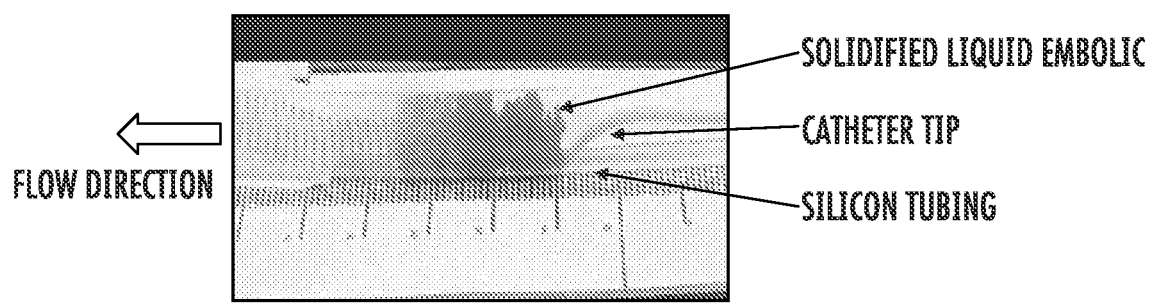
FIG. 11 illustrates catheter delivery of NIPAAM-DBA-NIPAAM/polyAMPS complex into a flow model (PBS media, 37° C.), in accordance with an embodiment of the present disclosure. In the flow model a foam pad is held in place within the polymer tubing by a spring which maintains the foam against the flow of PBS.

Solutions of the NIPAAM-DBA-NIPAAM triblock copolymer prepared at low temperature and pH 5-6 could also be easily delivered through a catheter as a liquid embolic composition (FIG. 11). During catheter delivery in a PBS flow model system the polymer solution tended to begin to gel within the catheter as the temperature rose from ambient temperature to 37° C. Nonetheless, the gel remains pushable without undue force, and this allows rapid gelling with an appropriate gel strength (i.e., without being sheared to fragments) after entering the blood flow. When saline started to exchange with the water in gel, the gel pH increased to pH 7 causing the deprotonation of DBA and enhanced gel strength resulting in favorable long term gel stability.

Radiopaque contrast medium and tantalum powder may be added into the composition to facilitate the operation procedure under fluoroscopic guidance. For example, liquid contrast medium, for instance, an iodinated oil such as ethiodized poppyseed oil, may also be used to confirm the quality of embolization. This can be easily achieved for example using a three way stop cock attached to the syringe proximally to the catheter so that contrast can be injected once embolization is complete.

EXAMPLE 13

Preclinical Test of a Complex Gel in Swine Kidney and Liver Model

To evaluate the deliverability, handling, embolization performance, and visibility of the complex gel in a swine model, Sample 4 (Table 3) and a reference sample (containing gelatin, laponite and tantalum mixed with water) were delivered into the arteries of kidney and liver.

Figure 12A:
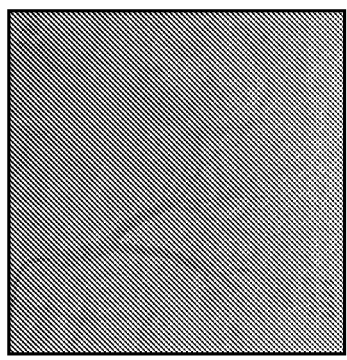
FIGS. 12A-12C show an embolization test of NIPAAM-DBA-NIPAAM/polyAMPS complex injected into a swine kidney model.
Figure 12B:
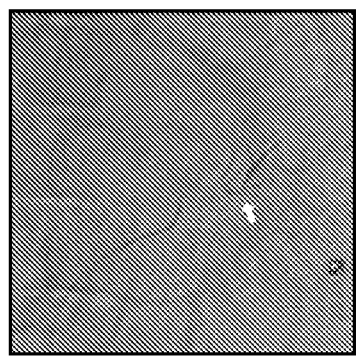
Figure 12C:
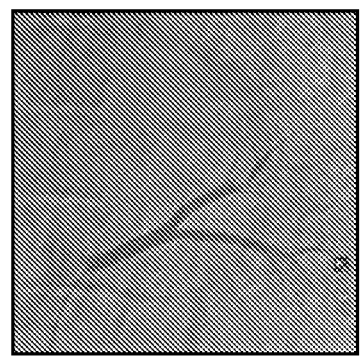
Figure 13A:
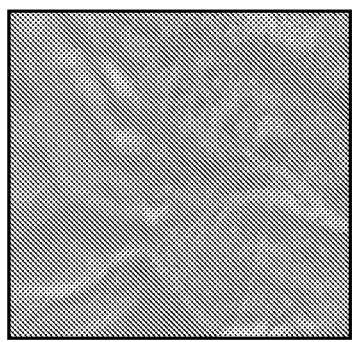
FIGS. 13A-13C show an embolization test of a reference composition injected into a swine kidney model, in accordance with an embodiment of the present disclosure.
Figure 13B:
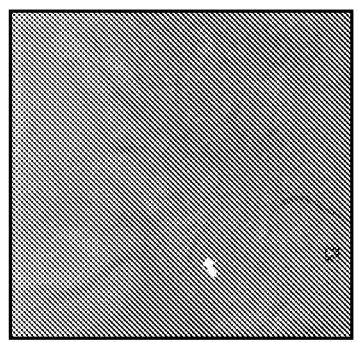
Figure 13C:
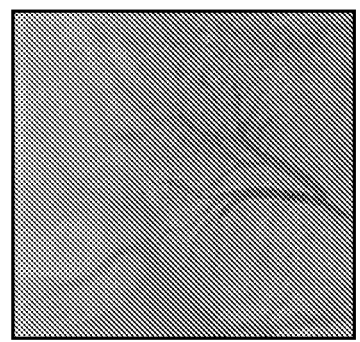

The gel sample in 18% concentration was first autoclaved in a 3 mL syringe at 121° C. for 30 min. Tests showed that the processed gel sample maintained its thermal and pH responsive gelation properties, and was not significantly different from the pre-autoclave sample. Preliminary observation according to physician's user experience were that the delivery of the sample was easy and without difficulty. The gel exiting the catheter tip appeared as a coil-like string, with a proximal distribution. Three vessels around 1.8-2.5 mm diameter were first embolized, followed by flushes of contrast medium which demonstrated good embolization efficiency. Embolization of deep vessels were also successful (FIGS. 12A-12C). The test showed better visibility of the gel under fluoroscope compared to the reference sample (FIGS. 13A-13C).

EXAMPLE 14

Drug Addition to and Release from the Complex Gel Liquid Embolic Formulation Doxorubicin solution (25 mg/mL) was fully mixed with the aqueous solution of the triblock copolymer (20%) by pushing through 3-way stopcock between two syringes. Following delivery into PBS at 37° C., the drug-loaded and solidified embolic hydrogel started to release doxorubicin gradually. After 24 hours, the solution was red indicating drug release. The solution was then replaced with fresh PBS at 37° C., which became red again after 24 hours, indicated a continuation of drug release.

What is claimed is:

1. A composition for medical use comprising an aqueous solution of a block copolymer that comprises one or more poly(N-isopropylamino acrylamide) blocks and one or more poly(2-(di-($C_{3-5}$)alkylamino)ethyl methacrylate) blocks, wherein each $C_{3-5}$ alkyl group is independently selected from propyl, butyl and pentyl groups, wherein the composition is in liquid form at 25° C.

2. The composition of claim 1, wherein the one or more poly(2-(di-($C_{3-5}$)alkylamino)ethyl methacrylate) blocks are poly(2-(dibutylamino)ethyl methacrylate) blocks.

3. The composition of claim 1, wherein the composition has a pH ranging from 5 to 6.

4. The composition of claim 1, wherein the composition becomes a gel when injected into phosphate buffered saline having pH 7.4 and a temperature of 37° C.

5. The composition of claim 1, wherein the composition becomes a gel when injected into a vasculature of a patient.

6. The composition of claim 1, wherein the block copolymer is a triblock copolymer having two poly(N-isopropylamino acrylamide) blocks and one poly(2-(di-($C_{3-5}$)alkylamino)ethyl methacrylate) block, or wherein the block copolymer is a triblock copolymer having one poly(N-isopropylamino acrylamide) block and two poly(2-(di-($C_{3-5}$)alkylamino)ethyl methacrylate) blocks.

7. The composition of claim 1, wherein the each of the one or more poly(N-isopropylamino acrylamide) blocks in the bock copolymer ranges from 5 to 600 monomer units in length.

8. The composition of claim 1, wherein each of the one or more poly(2-(di-($C_{3-5}$)alkylamino)ethyl methacrylate) blocks in the bock copolymer ranges from 50 to 300 monomer units in length.

9. The composition of claim 1, wherein a number average molecular weight of the block copolymer ranges from 2000 to 500,000 Da.

10. The composition of claim 1, wherein the composition has a viscosity ranging from 10 mPa's to 5000 mPa's when measured at a shear rate 50 1/s at a temperature of 25° C.

11. The composition of claim 1, wherein the block copolymer further comprises an additional polymer block ranging from 1 to 500 monomer units in length that comprises amine groups.

12. The composition of claim 1, further comprising an anionic polymer that comprises negatively charged groups selected from sulfonate groups, sulfate groups, phosphate groups, phosphonate groups and carboxylate groups.

13. The composition of claim 12, wherein the anionic polymer has a number average molecular weight ranging from 1000 to 5,000,000 Da.

14. The composition of claim 12, wherein the anionic polymer is present in an amount ranging from 0.1 to 50% wt/wt with respect to the weight of the composition.

15. The composition of claim 12, wherein the anionic polymer is selected from sulfonate polymers, polyphosphates, poly(carboxylic acids) and negatively charged polysaccharides.

16. The composition of claim 12, wherein the anionic polymer is poly(2-acrylamido-2-methylpropane sulfonate).

17. The composition of claim 1, further comprising an imaging agent or a therapeutic agent.

18. The composition of claim 1, wherein the composition is provided in a vial or syringe barrel.

19. A method comprising delivering the composition of claim 1 into a patient.

20. The method of claim 19, wherein the method is a method of treatment and wherein the composition is delivered into a vasculature of the patient.

* * * * *